(12) United States Patent
Sanchez Martin et al.

(10) Patent No.: US 11,510,995 B2
(45) Date of Patent: Nov. 29, 2022

(54) NANOSYSTEMS FOR CONTROLLED TRANSPORT OF ACTIVE MOLECULES FOR DIAGNOSTIC, PROGNOSTIC AND THERAPEUTIC PURPOSES

(71) Applicants: FIDIA FARMACEUTICI S.P.A., Abano Terme (IT); NANOGETIC S.L., Granada (ES)

(72) Inventors: Rosario Maria Sanchez Martin, Granada (ES); Salvatore Pernagallo, Granada (ES); Juan Diego Unciti Broceta, Cadiz (ES); Luciano Messina, Abano Terme (IT); Susanna Vaccaro, Abano Terme (IT); Laura Pilotto, Abano Terme (IT)

(73) Assignees: FIDIA FARMACEUTICI S.P.A., Abano Terme (IT); NANOGETIC S.L., Granada (ES)

( * ) Notice: Subject to any disclaimer, the term of this patent is extended or adjusted under 35 U.S.C. 154(b) by 65 days.

(21) Appl. No.: 16/061,220

(22) PCT Filed: Dec. 20, 2016

(86) PCT No.: PCT/IB2016/057824
§ 371 (c)(1),
(2) Date: Jun. 11, 2018

(87) PCT Pub. No.: WO2017/109696
PCT Pub. Date: Jun. 29, 2017

(65) Prior Publication Data
US 2018/0360990 A1  Dec. 20, 2018

(30) Foreign Application Priority Data

Dec. 21, 2015 (IT) ........................ 102015000085923

(51) Int. Cl.
| | | |
|---|---|---|
| A61K 47/69 | (2017.01) | |
| A61K 38/47 | (2006.01) | |
| A61K 9/19 | (2006.01) | |
| A61K 38/44 | (2006.01) | |
| A61K 38/48 | (2006.01) | |
| A61K 9/00 | (2006.01) | |
| A61K 9/10 | (2006.01) | |

(52) U.S. Cl.
CPC ............ *A61K 47/6933* (2017.08); *A61K 9/19* (2013.01); *A61K 38/446* (2013.01); *A61K 38/47* (2013.01); *A61K 38/4886* (2013.01); *A61K 47/6937* (2017.08); *A61K 47/6939* (2017.08); *A61K 9/0014* (2013.01); *A61K 9/0019* (2013.01); *A61K 9/0073* (2013.01); *A61K 9/10* (2013.01)

(58) Field of Classification Search
CPC ............ A61K 47/6937; A61K 47/6933; A61K 47/6939; A61K 9/19; A61K 38/446; A61K 38/4886; A61K 9/0014; A61K 9/0019; A61K 9/0073; A61K 9/10; A61K 38/47

See application file for complete search history.

(56) References Cited

U.S. PATENT DOCUMENTS

| | | | | |
|---|---|---|---|---|
| 7,767,429 | B2 * | 8/2010 | Bookbinder | ............ A61P 19/00 435/201 |
| 2008/0311182 | A1 * | 12/2008 | Ferrari | ................. A61K 9/1271 424/450 |
| 2015/0342883 | A1 * | 12/2015 | Cheng | .................. A61K 9/5153 424/1.37 |

FOREIGN PATENT DOCUMENTS

WO   WO-2014203133 A1 * 12/2014   ........... C12N 9/2474

OTHER PUBLICATIONS

Dingels, C et al. Squaric acid mediated chemoselective PEGylation of proteins: Reactivity of single-step-activated alpha-amino poly (ethylene glycol)s. Chem. Eur. J. 2012. 18: 16828-16835. (Year: 2012).*
Loos, C et al. Functinoalized polystyrene nanoparticles as a platform for studying bio-nano interactions. Beilstein Journal of Nanotechnology. 2014. 5: 2403-2412. Published Dec. 15, 2014. (Year: 2014).*
Thielbeer, F et al. Influence of spacer length on the cellular uptake of polymeric nanoparticles. Macromolecular Bioscience. 2013. 13:682-686. (Year: 2013).*
'FMOC-1-amino-4,7,10-trioxa-13-tridecanaminesuccinimic acid.' Chemical Book. 2017. [online]. Accessed on Mar. 12, 21. Retrieved from the Internet <URL: https://www.chemicalbook.com/ChemicalProductProperty_EN_CB0264569.htm> (Year: 2017).*
Hami et al., "Doxorubicin-conjugated PLA-PEG-Folate based polymeric micelle for tumor-targeted delivery: Synthesis and in vitro evaluation", DARU Journal of Pharmaceutical Sciences, Mar. 6, 2014, 7 pages, vol. 22, No. 1.
International Search Report for PCT/IB2016/057824 (PCT/ISA/210) completed on Mar. 23, 2017.
Rajan et al., "Hyaluronidase enzyme core-5-fluorouracil-loaded chitosan-PEG-gelatin polymer nanocomposites as targeted and controlled drug delivery vehicles", International Journal of Pharmaceutics, Jun. 21, 2013, pp. 514-522, vol. 453, No. 2.
Writted Opinion of the Interntional Searching Authority for PCT/IB2016/057824 (PCT/ISA/237) completed on Mar. 23, 2017.

* cited by examiner

Primary Examiner — Renee Claytor
Assistant Examiner — Susan E. Fernandez
(74) *Attorney, Agent, or Firm* — Birch, Stewart, Kolasch & Birch, LLP

(57) ABSTRACT

Disclosed is a nanoparticle system consisting of a polymer support or substrate in the form of nanoparticles to which a hydrolase enzyme able to degrade hyaluronic acid and one or more biologically and/or pharmacologically active molecules are covalently bonded, its preparation process and its uses in the diagnostic, prognostic and therapeutic fields.

6 Claims, 16 Drawing Sheets

X = Enzyme ingredient (hyaluronidase).

Y and Z = Substituent/variable groups

Sample scheme of covalent coupling of rHyal_Sk with polystyrene nanoparticles.

Enzyme activity of rHyal_Sk covalently coupled to nanoparticles (turbidimetric assay)

Non-linear curve of % activity of hyaluronidase/ Log [enzyme units]: X values interpolated Covalent bi-functionalisation of nanoparticles with rHyal_Sk and fluorophore or medicament Covalent bi-functionalisation of nanoparticles with rHyal_Sk and antibody (Ab)

A549

A. 24h

B. 96h

C

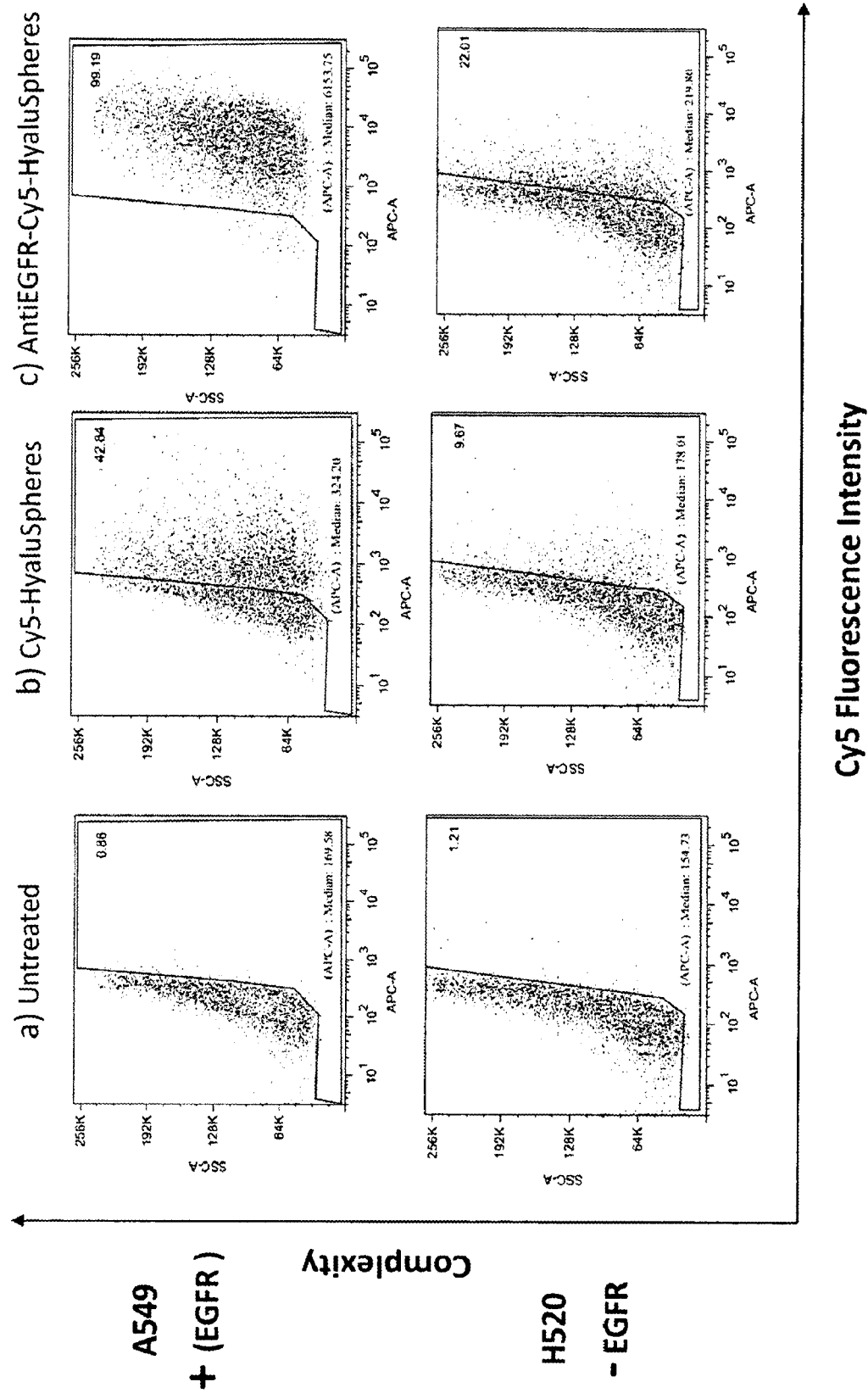

NANOSYSTEMS FOR CONTROLLED TRANSPORT OF ACTIVE MOLECULES FOR DIAGNOSTIC, PROGNOSTIC AND THERAPEUTIC PURPOSES

The invention relates to a nanoparticle system consisting of a polymer support or substrate in the form of nanoparticles to which a hydrolase enzyme able to degrade hyaluronic acid and one or more biologically and/or pharmacologically active molecules are covalently bonded, its preparation process and its uses in the diagnostic, prognostic and therapeutic fields.

PRIOR ART

The use of nanoparticles to transport medicaments through the circulatory system is a known technique, which is becoming increasingly widely used due to major technological progress in the field. It offers considerable advantages over conventional administration methods; when injected into the bloodstream, nanoparticles, propelled by haemodynamic actions, reach the site of the pathological process and, after adhering to the walls of the "sick" cell, release the medicament locally at the required dose; they consequently have a highly selective action. Nanoparticles are particles with nanometric dimensions, which usually consist of a carrying structure that contains the medicament or, more generally, an active molecule; nanoparticles should be designed in such a way that regardless of the chosen administration route, the release of the medicament associated with them is calibrated in both qualitative and quantitative terms to provide:

a) high selectivity, only detecting and acting against sick cells, or at the target site in general;
b) high efficacy, so that the minimum effective amount of the active molecule is used;
c) low toxicity, as a direct result of point b).

The studies conducted to date to evaluate nanoparticle systems demonstrate that they represent, in vitro, an effective administration route for medicaments and/or active molecules; in vivo, however, consideration must be given to the ability of the nanoparticles to overcome the barriers inherent in each administration route, the distribution volume required to achieve the therapeutic effect, and above all the toxicity which may result; the size, type and composition of said particles must therefore be precisely calibrated in relation to the intended applications. For the most common administration routes (oral, injection), the most critical factors are associated with the fact that the nanoparticles may release too much or too little of the active ingredient, becoming toxic in the first case and useless in the second; moreover, after oral administration, the hepatic first-pass effect can significantly affect the blood concentration needed for the pharmacological activity.

The need to control more directly and optimize the concentration of the medicament in the blood has led to the development of alternative administration systems through the skin (transdermal route) or the mucosa (transmucosal route, which comprises the sublingual/buccal, nasal, tracheal and rectal routes). Said systems enable the medicament to be introduced rapidly into the bloodstream, eliminating the risks and difficulties described above, since both skin and mucosa have a high density of blood vessels which allow rapid systemic diffusion of the medicament. Even in these cases, however, the natural barrier that the nanoparticles must cross must be considered; for example, the transcutaneous route requires the nanoparticles to penetrate the skin, and this problem has been dealt with to date by co-administration of the medicament with enzymes that promote said penetration, such as hyaluronidase. Hyaluronidase hydrolyses the hyaluronic acid present in the tissues, depolymerizing the viscoelastic structure of the subcutaneous interstitial matrix and thus increasing the dispersion of the locally injected nanoparticles (Bookbinder et al., J Contr Rel 2006, 28, 230-241). Some technical solutions that combine an active ingredient with hyaluronidase and with free polymers or polymers organized into micro- or nanoparticles are already known; however, said solutions are characterised in that the various ingredients are mixed together, or at most, the nanoparticles incorporate active ingredients and/or the enzyme hyaluronidase, which are inserted into the particles during the formation process (WO2013151774; U.S. 2013302400; Rajan et al., Int J Pharmac, 2013, 453, 514-522). However, with this process, the ingredients as a whole obviously cannot be precisely measured in order to achieve a constant, continuous release of active ingredient at the maximum therapeutic doses and with the minimum toxicity. In any event, said solutions do not ensure that the medicament and particle remain bonded until they reach their target site.

DESCRIPTION OF THE INVENTION

The present invention overcomes the current problems by using already structured nanoparticles which are bonded with covalent bonds to one or more active substances, in quantities calculated to ensure that they perform the desired function, and the enzyme hyaluronidase, which has the function of promoting penetration.

DESCRIPTION OF FIGURES

FIG. 14. Flow cytofluorometry data of cell penetration by nanosystems obtained as described in Example 4C on A549 and H520 cell lines.

DETAILED DESCRIPTION OF THE INVENTION

The nanoparticle system according to the invention consists of a polymer support or substrate in the form of nanoparticles to which a hydrolase enzyme able to degrade hyaluronic acid (hyaluronidase) and one or more biologically and/or pharmacologically active molecules are covalently bonded, its preparation process and its uses in the diagnostic, prognostic and therapeutic fields.

The nanoparticles according to the invention, due to the type of bond with which they are anchored to the target molecules, represent an innovative system for the transport and controlled, calibrated release of active ingredients, which simultaneously guarantees high selectivity, high efficacy and low toxicity.

Figure 1:
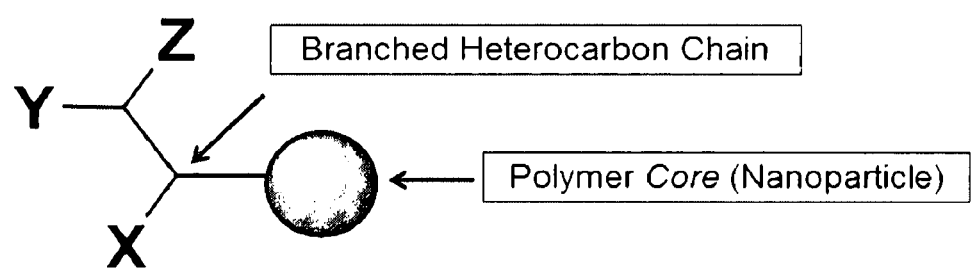
FIG. 1. Schematic structure of the nanosystem according to the invention consisting of a core polymer (nanoparticle) bonded to a branched carbon chain containing one or more groups suitable for covalent bonding of active molecules.

Unlike the systems currently known, all the ingredients of the nanoparticle system according to the invention are combined by means of stable covalent bonds to form a single nanosystem with hyaluronidase activity able to bind and transport other functionally active molecules; they are therefore no longer mechanically separable from one another, and operate as a single unit. The nanosystem described herein consists of a polymer core (nanoparticle) bonded to a branched heterocarbon chain containing one or more groups able to bond the target active constituents, in order to form a single active molecular entity, the structure of which is schematically illustrated in FIG. 1.

Polymer Core

The polymer core in the form of a nanobead consists of natural or synthetic polymers or copolymers comprising functional groups able to react with functional groups of the heterocarbon chain. Examples of polymers include polystyrene (PS) functionalised with amino groups, polylactic acid (PLA), polylactic coglycolic acid (PLGA), poly(N-vinylpyrrolidone) (PVP), polyethylene glycol (PEG), polycaprolactone, polyacrylic acid (PAA), polymethyl methacrylate and polyacrylamide. Examples of natural polymers which can be used to prepare the nanoparticles include chitosan, gelatin, sodium alginate and albumin. Particularly suitable for the purposes of the invention is polystyrene functionalised with amino groups, which is obtainable, for example, by a process of polymerization in dispersion (Sanchez-Martin et al, 2005, ChemBioChem, 6,1341-1345) from aqueous solutions of: a) styrene as main monomer; b) divinylbenzene (DVB), a crosslinking agent containing two vinyl groups; c) vinylbenzylamine hydrochloride (VBAH) as second monomer containing an amino group. The reaction is conducted at 80° C. in an inert atmosphere with magnesium sulphate as stabilising agent. A water-soluble radical initiator, 2-dihydrochloride-2"-azobis-(2-methylpropionamide) (V-50), is added 30 minutes after the start of the reaction. The reaction continues for a further 2 hours under stirring. Nanoparticles of dimensions ranging between 50 and 2000 nanometres are obtained in this way. Polystyrene nanoparticles of dimensions ranging between 100 and 500 nm, and in particular amounting to 200 nm, are preferred. The synthesis described was optimized to obtain 200 nm nanoparticles functionalised with amino groups. The dimensions were checked and the nanoparticles dispersed with laser diffractometry [Dynamic Light Scattering (DLS) Zetasizer Nano ZS, Malvern Instruments] and scanning electron microscopy (SEM, Hitachi, S-510).

Heterocarbon Chain

The branched heterocarbon chain (hereinafter called "carbon chain") contains one or more groups suitable to form a covalent bond with active molecules and simultaneously generates a space between the nanoparticle and said molecules. Said chains are variable-length chains having groups able to form covalent bonds, in particular groups orthogonal to one another, which are deprotected by various procedures during synthesis. Their presence improves biocompatibility and reduces the interactions between the nanoparticle and the active molecules, thus increasing the stability and functionality of the latter. Examples of said chains include chains saturated with a number of carbons ranging between 6 and 24; methoxypolyethylene glycol chains; dimethyl suberimidate chain; chains of polyalkyl glycols, in particular polyethylene glycols, among which the N-Fmoc-N-succinyl-4,7,10-trioxa-1,13-tridecanediamine chain (PEG spacer) is particularly preferred. The length of the chain can also be modified as required (steric bulk of the molecules to be bonded, reaction conditions, etc.) by adding spacers; polyethylene glycol (PEG) chains are generally used for this purpose.

Substituents: Group X

Group X (FIG. 1) represents the enzymatic component (hyaluronidase), which may be of human or animal origin, from vertebrates, bacteria or obtained in recombinant form. The hyaluronidase obtained by bacterial fermentation or recombinant techniques is preferred, such as hyaluronidase from *Streptomyces koganeiensis* ATCC 31394, in its recombinant form produced according to WO2014203133 (rHyal_Sk). Said hyaluronidase is highly stable and suitable for the processes required for covalent conjugation to nanoparticles. The presence of hyaluronidase in group X gives the system a hydrolytic capacity specific for hyaluronic acid.

Substituents: Groups Y and Z

They represent the variable part of the system, as they differ according to the intended applications of the nanoparticle system. According to the invention, "active molecules" means both small molecules and complex molecular structures (vaccines, antibodies, etc.). In general, group Y represents the active molecules, which may be actual medicaments of natural derivation (such as some 5-fluorouracil antitumorals, gemcitabine, doxorubicin, etc.), semi-synthetic, synthetic or recombinant medicaments, diagnostic agents, radioactive agents, antibodies, camel nano-antibodies, etc.), biologically active substances such as enzymes (e.g. human superoxide dismutase, native and/or modified microbial collagenase), proteins, peptides, hormones, growth factors, coagulation factors, cytokines, dyes, fluorophores (such as Cy3, Cy5, Cy7, fluorescein, rhodamine, naphthofluorescein, etc.), and in general any active substance which can be conjugated to a covalent bond. Group Z may be hydrogen (—H), an alkyl chain, a polyethylene glycol chain, sulphonic groups, directional molecules (antibodies, peptide chains, nucleic acids, polynucleotides, sense and antisense oligonucleotides, molecular conjugates containing RNA or DNA, water-soluble RNA, DNA vectors, natural, synthetic or recombinant vaccines) and other specific ligands (once again defined as "active molecules") to give the nanosystem selective properties.

Groups Y and Z can be variously combined with one another, depending on the effect to be given to the nanoparticle system, its intended purpose and its use.

Various functional groups and known methods can be used for the covalent conjugations, such as bonds mediated by glutaraldehyde molecules, active esters, bonds via maleimide, disulphide groups and squaric acid. The bond via diethyl squarate is particularly preferred for the bond with hyaluronidase.

Figure 2:
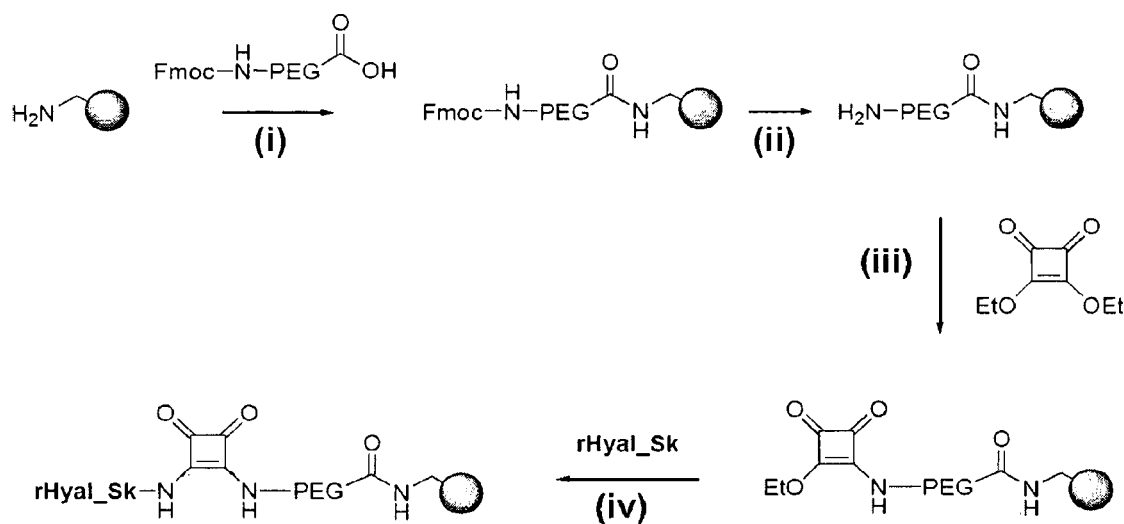
FIG. 2. Sample schema for covalent coupling of rHyal_sk to 200 nm polystyrene nanoparticles.
Figure 3:
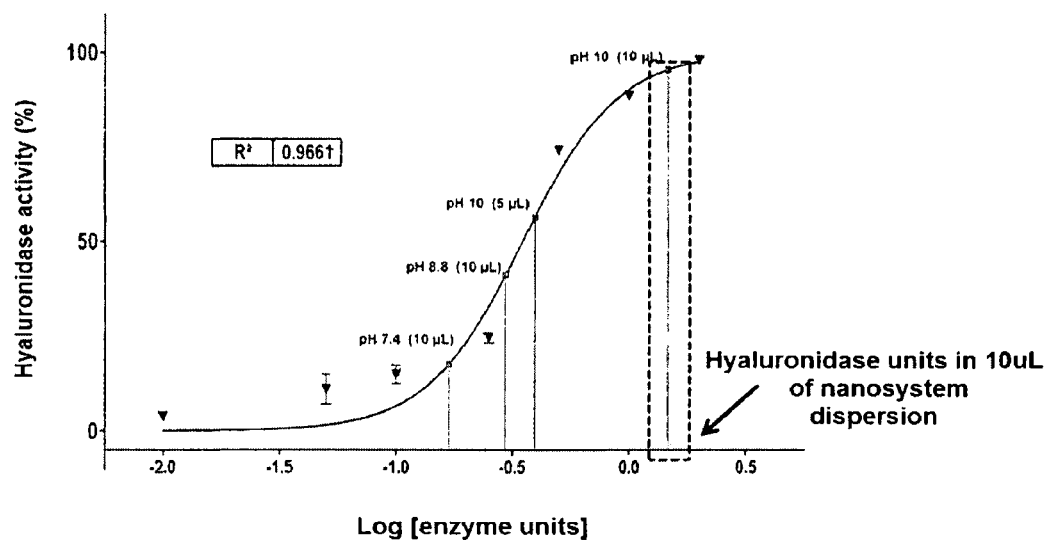
FIG. 3. Graph showing results of the enzymatic activity of rHyal_sk covalently bonded to nanoparticles (turbidimetric assay). The graph indicates the number of HYAL units coupled to the nanoparticles.

Schematically, the preparation process of the nanoparticle system according to the invention comprises:

1. functionalization of nanoparticles, preferably polystyrene nanoparticles, with suitable functional groups, especially primary or tertiary amino groups ($—NH_2$), carboxyl groups, epoxy groups, preferably amino groups;

2. functionalization of the particles thus obtained with the suitably selected heterocarbon chain which, due to its orthogonal groups, subsequently leads to precise, selective functionalizations; in this way the nanoparticles are given two or three temporarily protected arms which, after selective deprotection, are ready to receive the active molecules;

3. functionalization of the nanoparticle with hyaluronidase, preferably the recombinant type rHyal_Sk (group X), in a reaction medium with pH values ranging between 7 and 11, in particular pH=10, and through a covalent bond, preferably via diethyl squarate. At this pH value there are significant yields for the purpose of industrial scale-up (FIG. 2).

4. functionalization of the nanoparticle with one (bifunctionalization) or two (trifunctionalization) suitably selected active molecules, to obtain the system according to the invention.

Points 3 and 4 of the process thus schematically illustrated can be inverted, according to the dimensions, the nature of the molecules and their stability under the process conditions.

A further object of the invention consists of pharmaceutical compositions comprising the nanoparticle systems thus obtained, mixed with pharmaceutically acceptable excipients. The compositions according to the invention are typically in freeze-dried form for reconstitution, aqueous suspension or gel, and may be given by subcutaneous, intradermal, intrathecal, intramuscular, intraperitoneal, intravenous, intra-arterial, transdermal, transcutaneous or transmucosal administration or by inhalation, in particular by subcutaneous, intradermal, transcutaneous, transdermal, transmucosal or intramuscular administration or by inhalation.

The invention is described in greater detail in the examples below.

Example 1

Functionalization of Nanoparticles with Hyaluronidase rHyal_Sk 1. 1 mL of amino-functionalised polystyrene nanoparticles (solid content 2% in water) was centrifuged at 13400 rpm for 6 minutes, the supernatant was removed, and the nanoparticles were resuspended by sonication in 1 mL of N,N-dimethylformamide (DMF peptide grade, Scharlab).

2. N-Fmoc-N"-succinyl-4,7,10-trioxa-1,13-tridecane-diamine (PEG spacer, Sigma Aldrich) (75 equivalents) in DMF was mixed with 75 oxime equivalents (VWR) for 4 minutes at room temperature with continuous stirring (1400 rpm). 75 equivalents of N,N'-diisopropylcarbodiimide (DIC, Fluorochem) were then added, and the resulting mixture was placed under stirring (1400 rpm) for 2 minutes at room temperature.

3. This last solution (point 2) was added to the nanoparticles (point 1), and the resulting mixture was left to react by sonication and stirring (1400 rpm) at 60° C. for 2 hours [FIG. 2 (i)].

4. The nanoparticles were then centrifuged, the supernatant was removed, and the nanoparticles were washed with DMF (1 mL×2). After the washes the Fmoc group was removed with a 20% piperidine solution (Sigma Aldrich) in DMF (peptide grade, Scharlab) (1 mL×2) [FIG. 2 (ii)].

5. After deprotection, the nanoparticles were centrifuged at 13400 rpm for 6 minutes, the supernatant was removed and the nanoparticles were resuspended by sonication in 1 mL of a 1% solution of N,N-diisopropylethylamine (DIPEA, Sigma Aldrich) in absolute ethanol (Scharlab), water (1:1) (v/v). 75 equivalents of 3,4-diethoxy-3-cyclobutene-1,2-dione (diethyl squarate, Sigma Aldrich) were then added, and left to react under stirring (1400 rpm) at 25° C. for 15 hours [FIG. 2 (iii)].

6. The nanoparticles obtained were then centrifuged, and washed with deionised water after removal of the supernatant (1 mL×2).

The nanoparticles (point 6) were then centrifuged again, the supernatant was removed and the nanoparticles were resuspended in a 50 mM solution of sodium borate (1 mL) containing 100 µg of rHyal_Sk [FIG. 2 (iv)]. The nanoparticles were dispersed by sonication and a 1N solution of NaOH was added to maintain an environment at pH 10.

The final suspension was left to react under stirring (1400 rpm) at 25° C. for a further 15 hours. The nanoparticles were then centrifuged, the supernatant was removed and the nanoparticles were washed with: (1) a PBS 1×buffer at pH 7.4 (1 mL) followed by (2) a 1% solution of bovine serum albumin (BSA, Sigma) and 40 mM ethanolamine (Sigma) in PBS buffer (1 mL). The nanoparticles were preserved in a PBS 1×buffer at pH 7, at 4° C. (1 mL).

Example 2

Bifunctionalization of Nanoparticles with Hyaluronidase (rHyal_Sk) and a Fluorophore (Cy5)

Addition to the Nanoparticles of the Carbon Chain N-Fmoc-N"-Succinyl-4,7,10-Trioxa-1,13-Tridecane-Diamine (PEG Spacer, Sigma Aldrich)

1. 1 mL of functionalised amino nanoparticles (solid content 2% in water), prepared as described above, was centrifuged at 13400 rpm for 6 minutes, the supernatant was removed, and the nanoparticles were resuspended by sonication in 1 mL of N,N-dimethylformamide (DMF peptide grade, Scharlab).

2. N-Fmoc-N"-succinyl-4,7,10-trioxa-1,13-tridecan-diamine (PEG spacer, Sigma Aldrich) (75 equivalents) in DMF was mixed with 75 of oxime equivalents (VWR) for 4 minutes at room temperature with continuous stirring (1400 rpm). 75 equivalents of N,N'-diisopropylcarbodiimide (DIC, Fluorochem) were then added, and the resulting mixture was placed under stirring (1400 rpm) for 2 minutes at room temperature.

Figure 4:
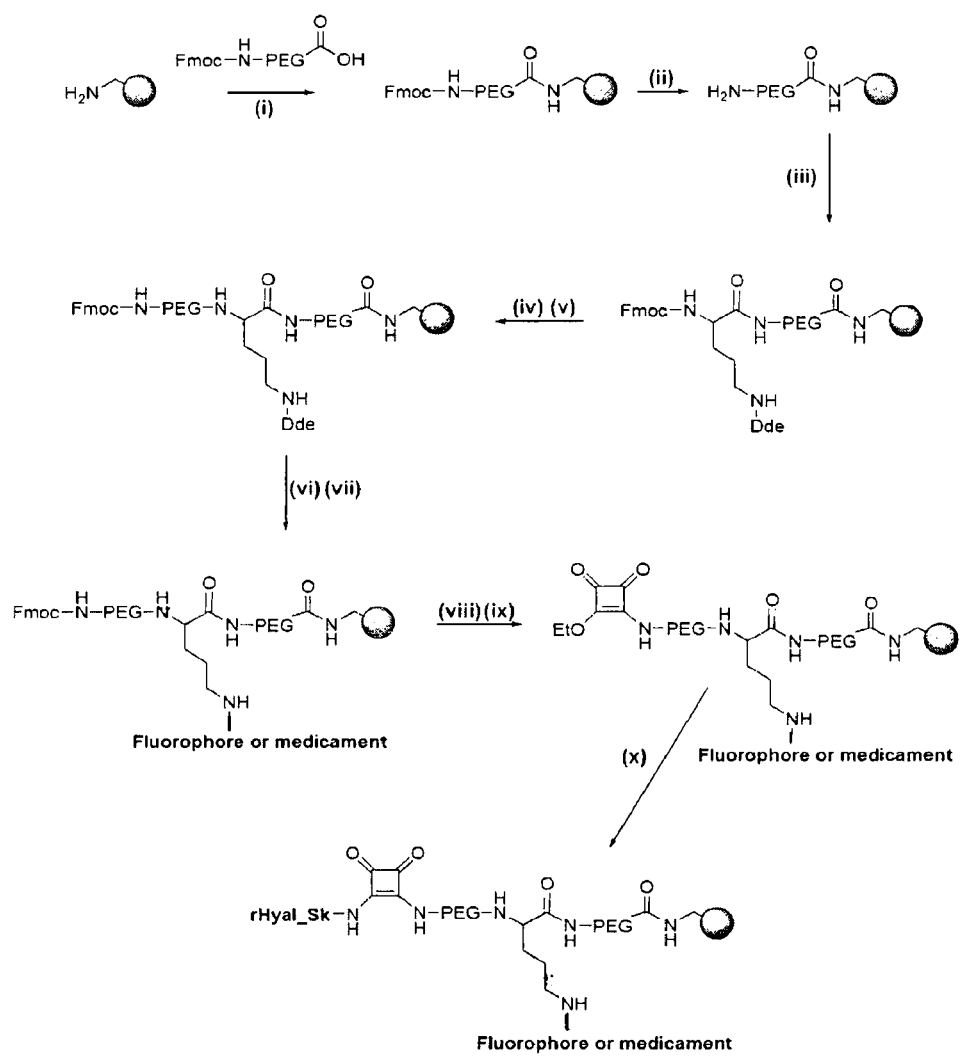
FIG. 4. Scheme portraying covalent bifunctionalization of nanoparticles with rHyal_Sk and fluorophore or medicament.

3. The solution described in point 2 was thus added to the nanoparticles (point 1), and the resulting mixture was left to react by sonication and stirring (1400 rpm) at 60° C. for 2 hours [FIG. 4 (i)].

4. The nanoparticles were then centrifuged, and after removal of the supernatant were washed with DMF (1 mL×2). After the washes the Fmoc group was deprotected with a 20% solution of piperidine (Sigma Aldrich) in DMF (peptide grade, Scharlab) (1 mL×2) [FIG. 4 (ii)].

5. After deprotection, the nanoparticles were centrifuged, the supernatant was removed and the nanoparticles were washed with DMF (1 mL×2) and methanol (synthesis grade, Scharlab) (1 mL×2). The nanoparticles were preserved in deionised water (1 mL) at 4° C.

Bifunctionalization with Fmoc and Dde Groups 6. 1 mL of nanoparticles with PEG spacer obtained as described in the preceding point (solid content 2% in water) (point 5) was centrifuged at 13400 rpm for 6 minutes, the supernatant was removed, and the nanoparticles were resuspended by sonication in 1 mL of DMF.

7. Fmoc-Lys (Dde)-OH (GLBiochem) (75 equivalents) in DMF was mixed with 75 oxime equivalents (VWR) for 4 minutes at room temperature under continuous stirring (1400 rpm). 75 equivalents of DIC (Fluorochem) were then added, and the resulting mixture was placed under stirring (1400 rpm) for 2 minutes at room temperature.

8. This last solution (point 7) was added to the nanoparticles (point 5), and the resulting mixture was left to react by sonication and stirring (1400 rpm) at 60° C. for 2 hours [FIG. 4 (iii)].

9. The nanoparticles were then centrifuged, and after removal of the supernatant were washed with DMF (1 mL×2). After the washes the Fmoc group was removed with a 20% solution of piperidine in anhydrous DMF (1 mL×2).

10. A PEG spacer was then added in the position previously protected by the Fmoc group, repeating the steps described in points 1-4 [FIG. 4 (iv-v)].

Conjugation of Fluorophore Cy5 to Nanoparticles 11. 1 mL of nanoparticles bifunctionalised with Fmoc and Dde, prepared as described in points 1-10 (solid content 2% in water), was centrifuged at 13400 rpm for 6 minutes, the supernatant was removed and the nanoparticles were resuspended by sonication in 1 mL of DMF. The Dde group was then selectively deprotected by treatment with hydroxylamine hydrochloride (1.80 mmol) (Acros)/imidazole (1.35 mmols) (Acros) in NMP:DMF (5:1) and stirring (1400 rpm) at 25° C. for 1 hour. 75 equivalents of sulpho-NHS ester Cy5 (Lumiprobe) were then added and left to react under stirring (1400 rpm) at 25° C. for 15 hours in the dark [FIG. 4 (vi-vii)].

12. After the 15-hour reaction, the nanoparticles were centrifuged, the supernatant was removed and the nanoparticles were washed with DMF (1 ml×2). Finally, the nanoparticles were preserved in deionised water (1 mL) at 4° C. in the dark.

Conjugation of rHyal_Sk to Nanoparticles

13. When the nanoparticles had been conjugated to Cy5, the Fmoc group was deprotected. The nanoparticles were centrifuged, and the supernatant removed and washed with DMF (1 ml×2). After the washes the Fmoc group was removed with a 20% solution of piperidine in DMF (1 ml×2) [FIG. 4 (viii)].

14. After deprotection, the nanoparticles were centrifuged at 13400 rpm for 6 minutes, the supernatant was removed and the nanoparticles were resuspended by sonication in 1 mL of a 1% solution of N,N-diisopropylethylamine (DIPEA, Sigma Aldrich) in absolute ethanol (Scharlab), water (1:1) (v/v). 75 equivalents of 3,4-diethoxy-3-cyclobutene-1,2-dione (diethyl squarate, Sigma Aldrich) were then added and left to react under stirring (1400 rpm) at 25° C. for 15 hours in the dark [FIG. 4 (ix)].

15. After the 15-hour reaction, the nanoparticles were centrifuged and washed with deionised water after removal of the supernatant (1 mL).

16. The nanoparticles (point 15) were then centrifuged again, the supernatant was removed and the nanoparticles were resuspended in a 50 mM solution of sodium borate (1 mL) containing 100 μg of rHyal_Sk [FIG. 4 (x)]. The nanoparticles were dispersed by sonication and a 1N solution of NaOH was added to maintain an environment at pH 10. The final suspension was left to react under stirring (1400 rpm) at 25° C. for a further 15 hours in the dark. After the 15-hour reaction, the nanoparticles were centrifuged, the supernatant was removed and the nanoparticles were washed with: (1) a PBS 1×buffer at pH 7.4 (1 mL) followed by (2) a 1% solution of bovine serum albumin (BSA, Sigma) and 40 mM ethanolamine (Sigma) in PBS buffer (1 mL). Finally, the nanoparticles were preserved in a PBS 1×buffer at pH 7, at 4° C. (1 mL) in the dark.

An identical procedure can be used to bond fluorophore Cy7, an analogous result being obtained.

Example 3

Bifunctionalization of Nanoparticles with rHyal_Sk and Capecitabine

Addition of the Carbon Chain N-Fmoc-N'''-Succinyl-4,7,10-Trioxa-1,13-Tridecane-Diamine to the Nanoparticles
See Example 2, points 1-5
Bifunctionalization with Fmoc and Dde Groups
See Example 2, points 6-10
Conjugation of Capecitabine to Nanoparticles 11. 1 mL of polystyrene nanoparticles bifunctionalised with Fmoc and Dde, prepared as described in points 1-10 (solid content 2% in water), was centrifuged at 13400 rpm for 6 minutes, the supernatant was removed and the nanoparticles were resuspended by sonication in 1 mL of DMF. The Dde group was then selectively deprotected by treatment with hydroxylamine hydrochloride (1.80 mmol)/imidazole (1.35 mmols) in NMP:DMF (5:1) and stirring (1400 rpm) at 25° C. for 1 hour [FIG. 4 (vi)]. An equimolar solution of succinic anhydride (75 equivalents) and DIPEA (75 equivalents) was then added, and dispersed by sonication and stirring (1400 rpm) at 60° C. for 2 h. Finally, the nanoparticles were washed with DMF (1 mL×2).

12. The nanoparticles thus obtained (succinic-NP) were activated by incubation with 200 μL of an equimolar solution of oxime (50 equivalents) and DIC (50 equivalents) for 4 hours, at room temperature, stirring at 1400 rpm. Capecitabine (Sigma Aldrich) (1 equivalent, 1 mg/100 L DMF) and DMAP (Sigma) (0.5 mL) were then added under stirring (1400 rpm) at room temperature for 12 hours [FIG. 4 (vii)]. After the reaction, the nanoparticles were centrifuged and washed with DMF (1 mL×2) and methanol (1 mL×2) after removal of the supernatant. The nanoparticles were preserved in deionised water (1 mL) at 4° C.

Conjugation of rHyal_Sk to Nanoparticles

13. When the nanoparticles had been conjugated to capecitabine, the Fmoc group was deprotected. The nanoparticles were centrifuged and washed with DMF (1 mL×2)

after removal of the supernatant. After the washes the Fmoc group was removed with a 20% solution of piperidine in anhydrous DMF (1 mL×2) [FIG. 4 (viii)].

14. After deprotection, the nanoparticles were centrifuged at 13400 rpm for 6 minutes, the supernatant was thus removed and the nanoparticles were resuspended by sonication in 1 mL of a 1% solution of N,N-diisopropylethylamine (DIPEA) in ethanol:water (1:1) (v/v). 75 equivalents of 3,4-diethoxy-3-cyclobutene-1,2-dione (diethyl squarate, Sigma Aldrich) were then added, and the resulting mixture was left to react under stirring (1400 rpm) at 25° C. for 15 hours [FIG. 4 (ix)].

15. After the 15-hour reaction, the nanoparticles were centrifuged, the supernatant was removed and the nanoparticles were washed with deionised water (1 mL).

16. The nanoparticles (point 15) were then centrifuged again, the supernatant was removed and the nanoparticles were resuspended in a 50 mM solution of sodium borate (1 mL) containing 100 µg of rHyal_Sk. The nanoparticles were dispersed by sonication and a 1N solution of NaOH was added to maintain an environment at pH 10. The final suspension was then left to react under stirring (1400 rpm) at 25° C. for a further 15 hours [FIG. 4 (x)]. After the 15-hour reaction the nanoparticles were centrifuged, the supernatant was removed and the nanoparticles were washed with a PBS 1×buffer at pH 7.4 (1 mL) followed by a 1% solution of bovine serum albumin (BSA) and 40 mM ethanolamine in PBS buffer (1 mL). The nanoparticles were preserved in a PBS 1×buffer at pH 7, at 4° C. (1 mL).

Example 3B

Bifunctionalization of Nanoparticles with rHyal_Sk and Doxorubicin (Doxo-Hyaluspheres)

Addition of the Carbon Chain N-Fmoc-N"-Succinyl-4,7,10-Trioxa-1,13-Tridecane-Diamine to the Nanoparticles
  Diamine to the Nanoparticles
  See Example 2, points 1-5
  Bifunctionalization with Fmoc and Dde Groups
  See Example 2, points 6-10
  Conjugation of Doxorubicin to Nanoparticles 11. 1 mL of nanoparticles bifunctionalised with Fmoc and Dde, prepared as described in points 1-10 (solid content 2% in water), was centrifuged at 13400 rpm for 6 minutes, the supernatant was removed and the nanoparticles were resuspended by sonication in 1 mL of DMF. The Dde group was then selectively deprotected by treatment with hydroxylamine hydrochloride (1.80 mmol)/imidazole (1.35 mmols) in NMP:DMF (5:1) and stirring (1400 rpm) at 25° C. for 1 hour [FIG. 4 (vi)]. An equimolar solution of succinic anhydride (75 equivalents) and DIPEA (75 equivalents) was then added, and dispersed by sonication and stirring (1400 rpm) at 60° C. for 2 h. Finally, the nanoparticles were washed with DMF (1 mL×2).

12. The nanoparticles thus obtained (succinic-NP) were activated by incubation with 200 µL of an equimolar solution of oxime (75 equivalents) and DIC (75 equivalents) for 4 hours, at room temperature, stirring at 1400 rpm. The nanoparticles were then centrifuged, the supernatant was removed and the nanoparticles were resuspended in a solution of hydrazine hydrate (55% solution in water), 75 equivalents in 1 mL of DMF. The nanoparticles were dispersed by sonication and left to react under stirring (1400 rpm) at 25° C. for 15 hours.

13. After the reaction the nanoparticles were washed with DMF, methanol and PBS at pH 7.4.

14. The nanoparticles (point 13) were then washed with PBS at pH 6 (3×1 mL) and resuspended in a solution of doxorubicin (5 equivalents) in PBS at pH 6 (1 mL). The nanoparticles were then dispersed by sonication and left to react under stirring (1000 rpm) at 50° C. for 15 hours.

15. After the reaction, the nanoparticles were centrifuged, and washed with PBS pH 7.4 (1 mL×2). The nanoparticles were preserved in PBS pH 7.4 (1 mL) at 4° C. [FIG. 4 (vii)]
  Conjugation of rHyal_Sk to Nanoparticles 16. When the nanoparticles had been conjugated to doxorubicin, the Fmoc group was deprotected. The nanoparticles were centrifuged and washed with DMF (1 mL×2) after removal of the supernatant. After the washes the Fmoc group was removed with a 20% solution of piperidine in anhydrous DMF (1 mL×2) [FIG. 4 (viii)].

17. After deprotection, the nanoparticles were centrifuged at 13400 rpm for 6 minutes, the supernatant was thus removed and the nanoparticles were resuspended by sonication in 1 mL of a 1% solution of N,N-diisopropylethylamine (DIPEA) in ethanol:water (1:1) (v/v). 75 equivalents of 3,4-diethoxy-3-cyclobutene-1,2-dione (diethyl squarate, Sigma Aldrich) were then added, and the resulting mixture was left to react under stirring (1400 rpm) at 25° C. for 15 hours [FIG. 4 (ix)].

18. After the 15-hour reaction, the nanoparticles were centrifuged, the supernatant was removed and the nanoparticles were washed with deionised water (1 mL).

19. The nanoparticles (point 18) were then centrifuged again, the supernatant was removed and the nanoparticles were resuspended in a 50 mM solution of sodium borate (1 mL) containing 100 µg of rHyal_Sk. The nanoparticles were dispersed by sonication and a 1N solution of NaOH was added to maintain an environment at pH 10. The final suspension was then left to react under stirring (1400 rpm) at 25° C. for a further 15 hours [FIG. 4 (x)]. After the 15-hour reaction, the nanoparticles were centrifuged, the supernatant was removed and the nanoparticles were washed with a PBS 1×buffer at pH 7.4 (1 mL) followed by a 1% solution of bovine serum albumin (BSA) and 40 mM ethanolamine in PBS buffer (1 mL). The nanoparticles were preserved in a PBS 1×buffer at pH 7, at 4° C. (1 mL).

Example 4

Figure 5A:
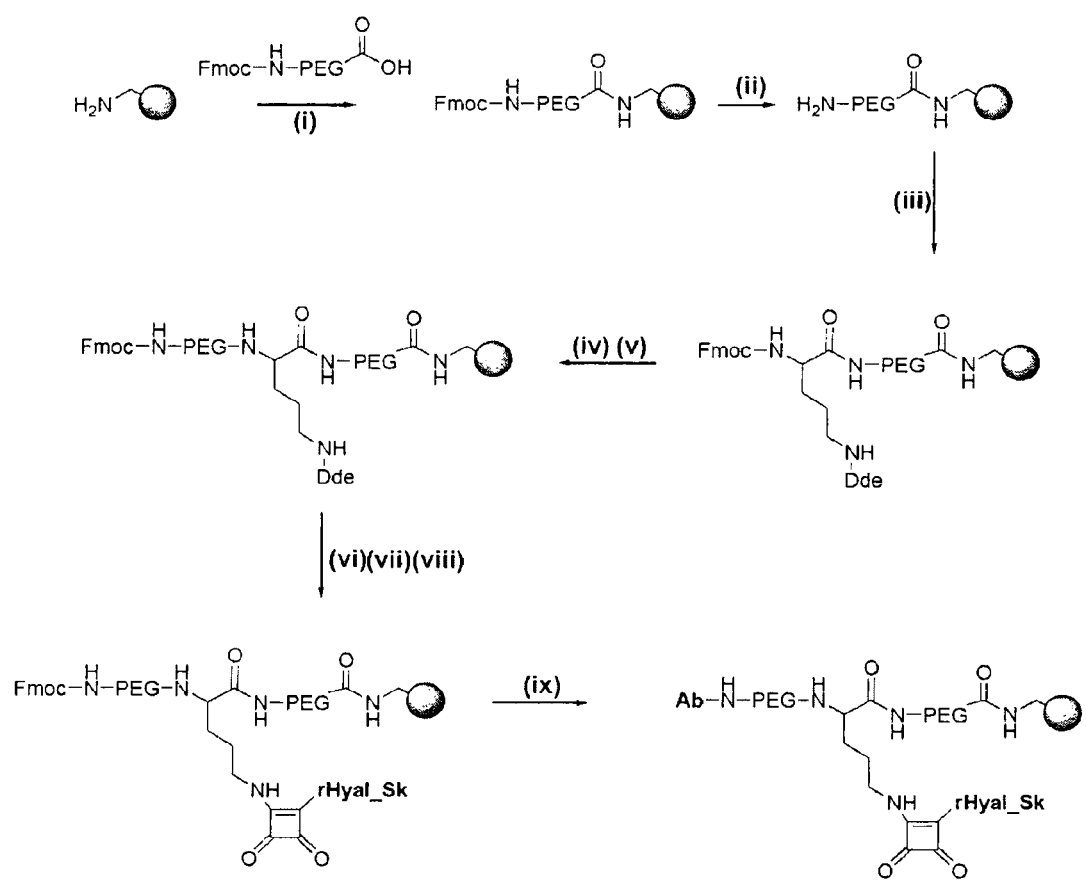
FIG. 5A. Scheme portraying covalent bifunctionalization of nanoparticles with rHyal_Sk and antibody (Ab).

Bifunctionalization of Nanoparticles with rHyal_Sk and an Anti-EGF Receptor Antibody Addition of Carbon Chain N-Fmoc-N-Succinyl-4,7,10-Trioxa-1,13-Tridecan-Diamine to the Nanoparticles
  See Example 2, points 1-5
  Bifunctionalization with Fmoc and Dde Groups
  See Example 2, points 6-10
  Conjugation of rHyal_Sk to Nanoparticles 11. 1 mL of nanoparticles bifunctionalised with Fmoc and Dde, prepared as described in points 1-10 (solid content 2% in water), was centrifuged at 13400 rpm for 6 minutes, the supernatant was removed and the nanoparticles were resuspended by sonication in 1 mL of DMF. The Dde group was then selectively deprotected by treatment with hydroxylamine hydrochloride (1.80 mmol)/imidazole (1.35 mmols) in NMP:DMF (5:1) and stirring (1400 rpm) at 25° C. for 1 hour [FIG. 5A (vi)]. The nanoparticles were then centrifuged at 13400 rpm for 6 minutes, the supernatant was removed and the nanoparticles were resuspended by sonication in 1 mL of a 1% solution of N,N-diisopropylethylamine (DIPEA) in ethanol:water (1:1) (v/v). 75 equivalents of 3,4-diethoxy-3-cyclobutene-1,2-dione (diethyl squarate, Sigma Aldrich)

were then added and left to react under stirring (1400 rpm) at 25° C. for 15 hours [FIG. 5A (vii)].

12. After the 15-hour reaction, the nanoparticles were centrifuged and washed with water (1 mL) after removal of the supernatant.

13. The nanoparticles (point 12) were then centrifuged again, the supernatant was removed and the nanoparticles were resuspended in a 50 mM solution of sodium borate (1 mL) containing 100 μg of rHyal_Sk [FIG. 5A (viii)]. The nanoparticles were dispersed by sonication and a 1N solution of NaOH was added to maintain an environment at pH 10. The final suspension was then left to react under stirring (1400 rpm) at 25° C. for a further 15 hours.

14. After the 15-hour reaction, the nanoparticles were centrifuged, the supernatant was removed, and the nanoparticles were washed with a PBS 1×buffer at pH 7.4 (1 mL) and then with a 1% solution of bovine serum albumin (BSA) and 40 mM ethanolamine in PBS buffer (1 mL). Finally, the nanoparticles were preserved in a PBS 1×buffer at pH 7, at 4° C. (1 mL).

Conjugation of Anti-EGF Receptor Antibody to Nanoparticles

15. When the nanoparticles had been conjugated to rHyal_Sk, the Fmoc group was deprotected. The nanoparticles were centrifuged and washed with DMF (1 mL×2) after removal of the supernatant. After the washes the Fmoc group was removed with a 20% solution of piperidine in DMF (1 mL×2).

16. 1 mL of nanoparticles (solid content 2% in water) was centrifuged at 13400 rpm for 6 minutes, the supernatant was removed, and the nanoparticles were resuspended by sonication in 1 mL of DMF. The following solutions were then added: a) LC-SPDP (Thermo Scientific) 1 mg/mL in DMF (dispersed by sonication), followed by (b) 20 equivalents of DIPEA. The resulting mixture was left under stirring (1400 rpm) at 25° C. for 12 hours. After 12 hours, a 1M solution of DTT was added, and the resulting mixture was further incubated for 3 hours at 25° C. under stirring (1400 rpm).

17. After the 3-hour reaction the nanoparticles were centrifuged, and washed with water after removal of the supernatant (1 mL×2).

18. An activated SMCC antibody (Monoclonal Anti-EGF Receptor antibody, Sigma Aldrich) was then added at the concentration of (1.5 mg/mL) and incubated for 3 hours, under stirring (1400 rpm) at 25° C. [FIG. 5A (ix)].

19. After the reaction with the antibody, the nanoparticles were centrifuged, the supernatant was removed, and the nanoparticles were washed with water (1 mL×2). The nanoparticles were preserved in deionised water (1 mL) at 4° C.

The resulting nanosystems were characterised for fluorescence by fluorescence microscopy and flow cytofluorometry (when they contained a fluorophore), and for hyaluronidase activity, measured by turbidimetric assay in order to detect any variations in their intrinsic properties, as described in the following examples.

Example 4B

Bifunctionalization of Nanoparticles with rHyal_Sk and an Anti-EGF Receptor Antibody and Preparation for Trifunctionalization Addition of Carbon Chain N-Fmoc-N-Succinyl-4,7,10-Trioxa-1,13-Tridecan-Diamine to the Nanoparticles
See Example 2, points 1-5
Bifunctionalization with Fmoc and Dde Groups
See Example 2, points 6-10

Figure 5B:
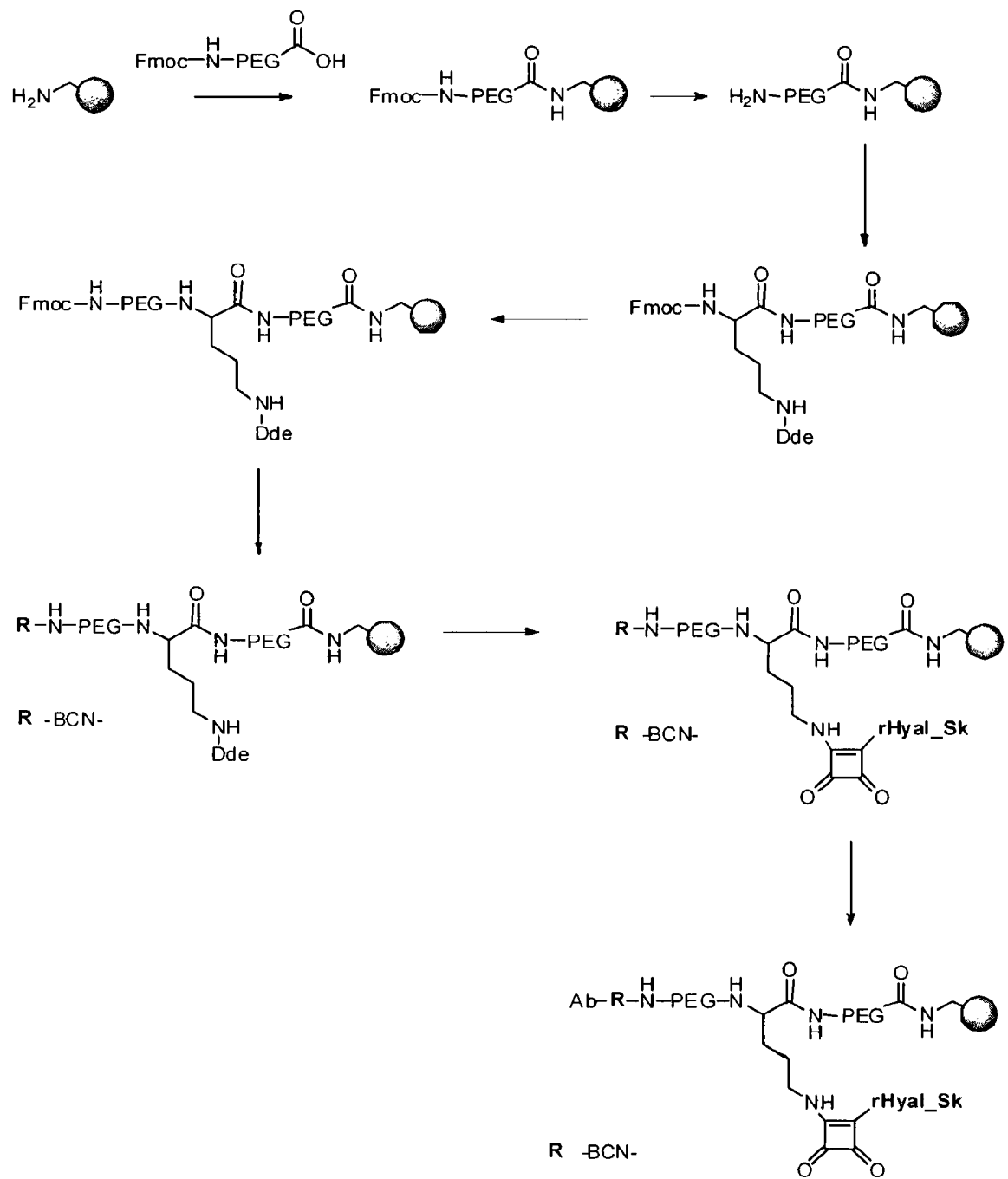
FIG. 5B. Scheme showing covalent bifunctionalization of nanoparticles with rHyal_Sk and antibody (Ab) and preparation for trifunctionalization.

Conjugation of (1R,8S,9S)—(1R,8S,9s)-Bicyclo[6.1.0] Non-4-yn-9-ylmethyl N-Succinimidyl Carbonate (BCN-NHS) for Trifunctionalization 11. 1 mL of nanoparticles bifunctionalised with Fmoc and Dde, prepared as described in points 1-10 (solid content 2% in water), was centrifuged at 13400 rpm for 6 minutes, the supernatant was removed and the nanoparticles were resuspended by sonication in 1 mL of DMF. The Fmoc group was then selectively deprotected by treatment with 20% piperidine in DMF (1 mL×2) [FIG. 5B (vi)].

12. The nanoparticles were washed with DMF (2 times) and dispersed by sonication, centrifuged at 13400 rpm for 6 minutes and the supernatant removed.

13. A solution of BCN-NHS (Sigma Aldrich) (2 equivalents) and DIPEA (1 equivalent) in DMF was prepared [FIG. 5B (vii)].

14. The solution (point 13) was added to the nanoparticles prepared in point 12, and the resulting mixture was sonicated and left to react under stirring at 1400 rpm, at 25° C., overnight [FIG. 5B (viii)].

15. After the reaction (point 14), the nanoparticles were centrifuged, the supernatant was removed and the nanoparticles were washed with DMF, methanol and water.

Conjugation of rHyal_Sk to Nanoparticles 16. 1 mL of nanoparticles bifunctionalised with BCN and Dde, prepared as described in points 1-15 (solid content 2% in water), was centrifuged at 13400 rpm for 6 minutes, the supernatant was removed, and the nanoparticles were resuspended by sonication in 1 mL of DMF. The Dde group was then selectively deprotected by treatment with hydroxylamine hydrochloride (1.80 mmol)/imidazole (1.35 mmols) in NMP:DMF (5:1) and stirring (1400 rpm) at 25° C. for 1 hour. The nanoparticles were then centrifuged at 13400 rpm for 6 minutes, the supernatant was removed and the nanoparticles were resuspended by sonication in 1 mL of a 1% solution of N,N-diisopropylethylamine (DIPEA) in ethanol: water (1:1) (v/v). 75 equivalents of 3,4-diethoxy-3-cyclobutene-1,2-dione (diethyl squarate, Sigma Aldrich) were then added, and left to react under stirring (1400 rpm) at 25° C. for 15 hours [FIG. 5B (ix)].

17. After the 15-hour reaction, the nanoparticles were centrifuged and washed with water (1 mL) after removal of the supernatant.

18. The nanoparticles (point 17) were then centrifuged, the supernatant was removed and the nanoparticles were resuspended in a 50 mM solution of sodium borate (1 mL) containing 100 μg of rHyal_Sk. The nanoparticles were dispersed by sonication and a 1N solution of NaOH was added to maintain an environment at pH 10. The final suspension was then left to react under stirring (1400 rpm) at 25° C. for a further 15 hours [FIG. 5B (x)].

19. After the 15-hour reaction, the nanoparticles were centrifuged, the supernatant was removed, and the nanoparticles were washed with a PBS 1×buffer at pH 7.4 (1 mL) and then with a 1% solution of bovine serum albumin (BSA) and 40 mM ethanolamine in PBS buffer (1 mL). Finally, the nanoparticles were preserved in a PBS 1×buffer at pH 7, at 4° C. (1 mL).

Conjugation of Anti-EGF Receptor Antibody to Nanoparticles

20. The nanoparticles prepared in point 19 were centrifuged, and the supernatant removed. At this point, a previously activated Ac-N₃ solution (Monoclonal Anti-EGF Receptor antibody, Sigma Aldrich) was added. The mixture was incubated for 15 hours under stirring (1000 rpm) at 25° C.

21. After the reaction with the antibody, the nanoparticles were centrifuged, the supernatant was removed, and the nanoparticles were washed with PBS (1 mL×2). The nanoparticles were preserved in PBS (1 mL) at 4° C. [FIG. 5B (xi)].

The nanosystems obtained were characterised for coupling and antibody specificity by gel electrophoresis and flow cytofluorometry, and for hyaluronidase activity, which was measured by turbidimetric assay to detect any variations in their intrinsic properties, according to the following examples.

Example 4C

Tri-Functionalization of Nanoparticles with a Fluorophore, rHyal_Sk and an Anti-EGF Receptor Antibody Addition of the Carbon Chain N-Fmoc-N"-Succinyl-4,7,10-Trioxa-1,13-Tridecane-Diamine to the Nanoparticles
See Example 2, points 1-5
Bifunctionalization with Fmoc and Dde Groups
See Example 2, points 6-10
Conjugation of (1R,8S,9S)-(1R,8S,9s)-Bicyclo[6.1.0]non-4-yn-9-ylmethyl N-succinimidyl Carbonate (BCN-NHS) for Trifunctionalization
See Example 4B, points 11-15

Figure 5C:
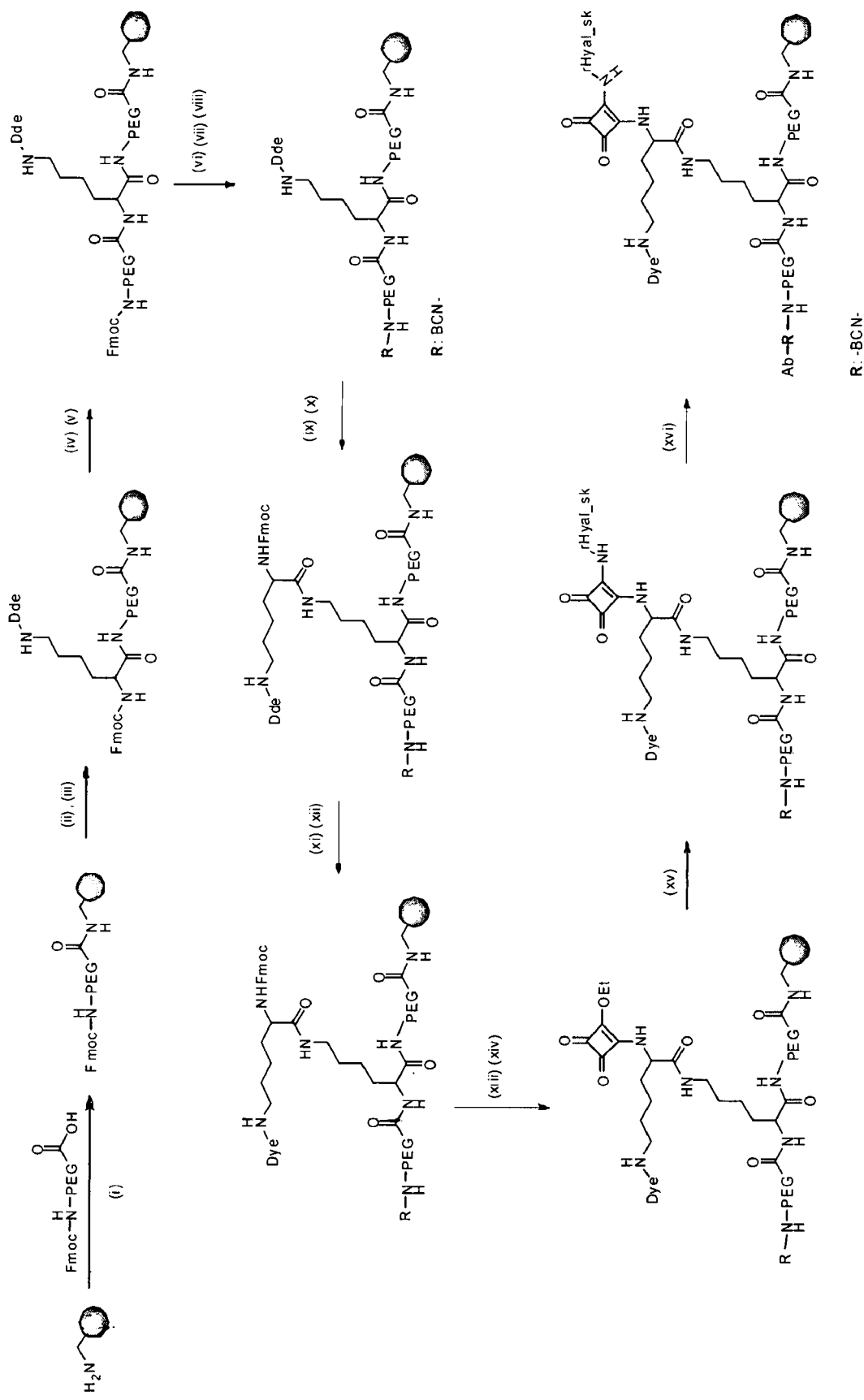
FIG. 5C. Scheme showing covalent trifunctionalization of nanoparticles with fluorophore, rHyal_Sk and antibody (Ab).

16. 1 mL of polystyrene nanoparticles bifunctionalised with BCN and Dde, prepared as described in points 1-15 (solid content 2% in water), was centrifuged at 13400 rpm for 6 minutes, the supernatant was removed and the nanoparticles were resuspended by sonication in 1 mL of DMF. The Dde group was then selectively deprotected by treatment with hydroxylamine hydrochloride (1.80 mmol)/imidazole (1.35 mmols) in NMP:DMF (5:1) and stirring (1400 rpm) at 25° C. for 1 hour [FIG. 5C (ix)].

17. Fmoc-Lys (Dde)-OH (GLBiochem) (75 equivalents) in DMF was mixed with 75 oxime equivalents (V WR) for 4 minutes at room temperature under continuous stirring (1400 rpm). 75 equivalents of DIC (Fluorochem) were then added, and the resulting mixture was placed under stirring (1400 rpm) for 2 minutes at room temperature.

18. This last solution (point 17) was added to the nanoparticles (point 16), and left to react by sonication and stirring (1400 rpm) at 60° C. for 2 hours [FIG. 5C (x)].

Conjugation of Fluorophore Cy5 to Nanoparticles 19. 1 mL of nanoparticles trifunctionalised with Fmoc and Dde, prepared as described in points 1-18 (solid content 2% in water), was centrifuged at 13400 rpm for 6 minutes, the supernatant was removed and the nanoparticles were resuspended by sonication in 1 mL of DMF. The Dde group was then selectively deprotected by treatment with hydroxylamine hydrochloride (1.80 mmol) (Acros)/imidazole (1.35 mmols) (Acros) in NMP:DMF (5:1) and stirring (1400 rpm) at 25° C. for 1 hour. 75 equivalents of sulpho-NHS ester Cy5 (Lumiprobe) were then added and left to react under stirring (1400 rpm) at 25° C. for 15 hours in the dark [FIG. 5C (xi-xii)].

20. After the 15-hour reaction, the nanoparticles were centrifuged, the supernatant was removed and the nanoparticles were washed with DMF (1 ml×2). Finally, the nanoparticles were preserved in deionised water (1 mL) at 4° C. in the dark.

Conjugation of rHyal_Sk to Nanoparticles

21. When the nanoparticles had been conjugated to Cy5, the Fmoc group was deprotected. The nanoparticles were centrifuged, the supernatant was removed and the nanoparticles were washed with DMF (1 ml×2). After the washes the Fmoc group was deprotected with a 20% solution of piperidine in DMF (1 ml×2) [FIG. 5C (xiii)].

22. After deprotection, the nanoparticles were centrifuged at 13400 rpm for 6 minutes, the supernatant was removed and the nanoparticles were resuspended by sonication in 1 mL of a 1% solution of N,N-diisopropylethylamine (DIPEA, Sigma Aldrich) in absolute ethanol (Scharlab) and water (1:1) (v/v). 75 equivalents of 3,4-diethoxy-3-cyclobutene-1,2-dione (diethyl squarate, Sigma Aldrich) were then added and left to react under stirring (1400 rpm) at 25° C. for 15 hours in the dark [FIG. 5C (xiv)].

23. After the 15-hour reaction, the nanoparticles were centrifuged, the supernatant was removed and the nanoparticles were washed with deionised water (1 mL). The nanoparticles (point 22) were then centrifuged again, the supernatant was removed and the nanoparticles were resuspended in a 50 mM solution of sodium borate (1 ml) containing 100 µg of rHyal_Sk [FIG. 5C (xv)]. The nanoparticles were dispersed by sonication and a 1N solution of NaOH was added to maintain an environment at pH 10. The final suspension was then left to react under stirring (1400 rpm) at 25° C. for a further 15 hours in the dark. After the 15-hour reaction, the nanoparticles were centrifuged, the supernatant was removed and the nanoparticles were washed with (1) a PBS 1×buffer at pH 7.4 (1 mL) followed by (2) a 1% solution of bovine serum albumin (BSA, Sigma) and 40 mM ethanolamine (Sigma) in PBS buffer (1 mL). Finally, the nanoparticles were preserved in a PBS 1×buffer at pH 7, at 4° C. (1 mL).

Identical methods can be used to bond fluorophore Cy7, and a similar result will be obtained.

Conjugation of Anti-EGF Receptor Antibody to Nanoparticles

24. The nanoparticles prepared in point 23 were centrifuged, and the supernatant removed. At this point, a previously activated Ac-N₃ solution (Monoclonal Anti-EGF Receptor antibody, Sigma Aldrich) was added. The mixture was incubated for 15 hours under stirring (1000 rpm) at 25° C. After the reaction with the antibody, the nanoparticles were centrifuged, the supernatant was removed, and the nanoparticles were washed with PBS (1 mL×2). The nanoparticles were preserved in PBS (1 mL) at 4° C. [FIG. 5 C (xvi)].

The nanosystems obtained were characterised for antibody coupling by gel electrophoresis, and for antibody specificity and fluorescence (fluorophore coupling) by flow cytofluorometry. Hyaluronidase activity was measured by turbidimetric assay to detect any variations in their intrinsic properties, according to the following examples.

Example 5

Evaluation of Enzyme Activity of rHyal_Sk After Functionalization with Nanoparticles as Described in Example 1

The enzymatic activity of the nanosystem was measured by turbidimetric determination conducted on the excess supernatant recovered from the preparation stages of Example 1, according to the following protocol.

Preparation of Reaction Buffers

1. Substrate Buffer (0.05% Solution of Hyaluronic Acid (w/v)).

Prepare an 0.5 mg/mL solution of hyaluronic acid in 300 mM of phosphate buffer (pH 5.35). Heat the solution to 95° C. under stirring at 500 rpm for 30 minutes (the time required to solubilise the hyaluronic acid). Then cool the solution to 37° C. and maintain it at 37° C. (until use).

Dilution Buffer (Enzyme).

Phosphate buffer (30 mM) containing 0.82% sodium chloride (pH 7.0, 37° C.)

2. Horse Serum Solution.

24 mM of sodium acetate and 79 mM of acetic acid containing 30% (v/v) horse serum (pH 3.75, 25° C.).

A. Preparation of standard curve.

The blank used is prepared with a mixture of 100 mL substrate buffer and 100 µL enzyme dilution buffer (see points 1 and 2 above).

The master solution is prepared by adding 4 µL standard bovine hyaluronidase (1 unit per mL) to 196 µL enzyme dilution buffer. Six 1:1 (v/v) serial dilutions are performed for the preparation of the curve.

B. Preparation of nanosystem suspension (nanoparticles covalently conjugated to the enzyme rHyal_sk). 10 µL of suspension is mixed with 90 µl of enzyme dilution buffer and 100 ml of substrate buffer.

C. Incubate for 30 minutes at 37° C., stirring at 500 rpm.

D. Add 400 µL of horse serum solution (point 3).

E. Incubate for 30 minutes at 37° C., stirring at 500 rpm. Measure the optical density at 640 nm.

The results of the turbidimetric analysis demonstrate that the enzyme retains hyaluronidase activity of around 97%. This confirms the efficiency of the system and demonstrates the high stability of rHyal_Sk even after the process of coupling to the nanoparticles.

Example 6

Evaluation of Activity of the Nanosystem Obtained from Example 2 (rHyal_Sk and Fluorophore Cy5)

Figure 6:
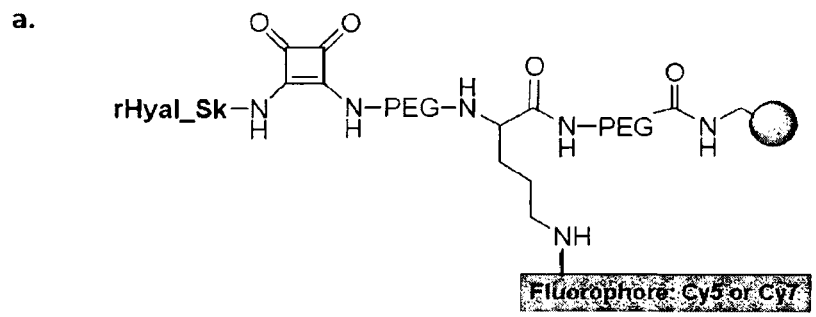
FIG. 6. Validation of nanosystems labelled with Cy5 and Cy7. a) General chemical structure; b) flow cytofluorometry data of nanosystems labelled with Cy5 and Cy7.
Figure 6:
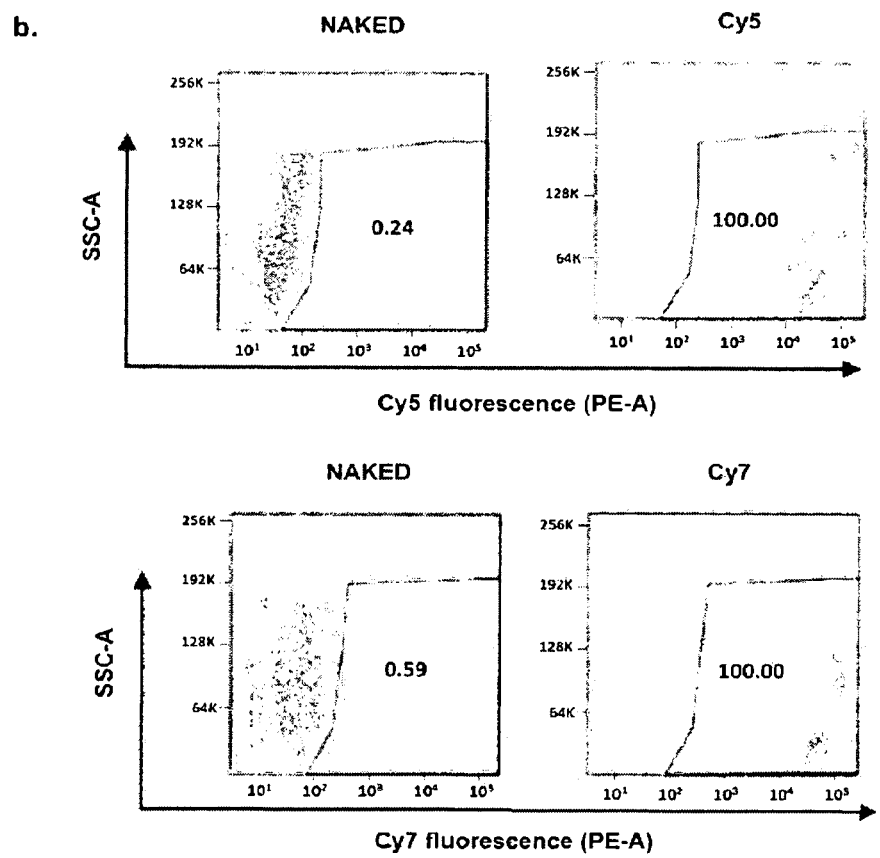

The fluorescence and hyaluronidase activity of the nanosystem of Example 2 were evaluated (FIG. 6A).

1 mL of nanosystem suspension was centrifuged and resuspended in 100 µL of water. 5 µL of the latter solution was then diluted in 100 µL for the flow cytometry studies. The flow cytometry was conducted with a FACSCanto II (Becton Dickinson & Co., N.J., USA) flow cytometer, using an excitation laser at 633 nm. Unconjugated nanoparticles were used as negative control. A Nikon A1R+/A1+ confocal laser microscope system was used for the confocal microscopy analysis. http://www.nikoninstruments.com/Information-Center/Confocal Unconjugated nanoparticles were used as negative control.

Figure 7:
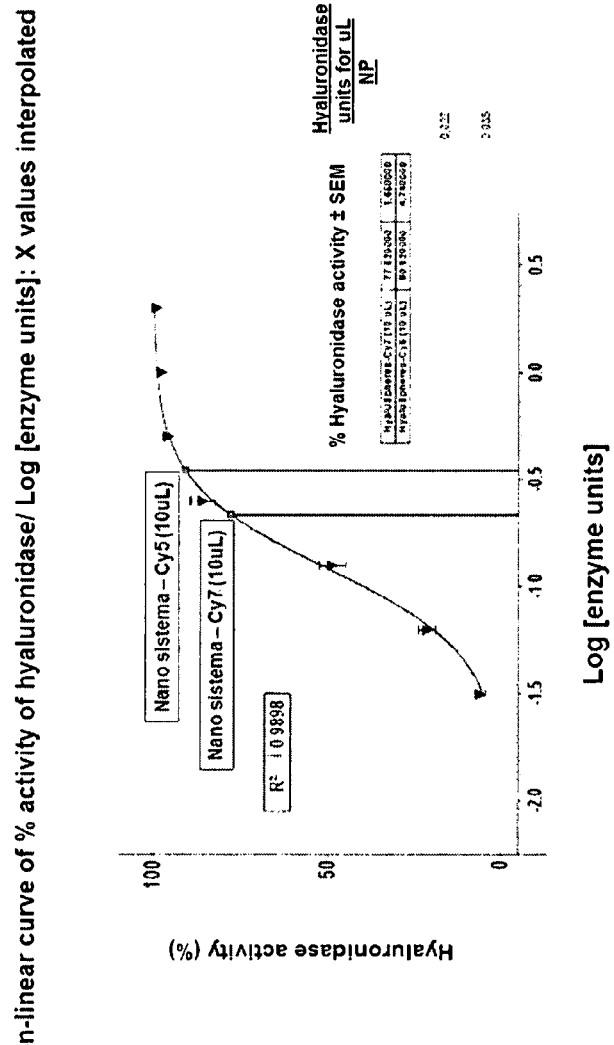
FIG. 7. Graph showing results of enzymatic activity of nanosystems bifunctionalised with rHyal_Sk and fluorophores (Cy5 and Cy7) (turbidimetric assay).

The microscopy and cytofluorometry data demonstrate its high level of fluorescence (FIG. 6B, C). Moreover, the turbidimetric data indicate a high level of hyaluronidase activity of the labelled nanosystems (FIG. 7). It can be concluded from both types of data that the two ingredients covalently coupled to the same nanoparticle retain their respective fluorescence and enzyme activities intact. Similar findings are obtained with the nanosystem carrying rHyal_Sk and fluorophore Cy7.

Example 7

Evaluation of Penetration of the Compounds Described in Example 2 in Cell Models In Vitro 3 different models were used to simulate subcutaneous absorption of the nanosystems.

Model 1: Penetration of Cell Monolayers

Nanoparticles prepared as described in Example 2 (Cy5-HyaluSpheres) were tested in this study, and nanoparticles conjugated to fluorophore Cy5 only (Cy5-FluoroSpheres) were used as control. Cells that play a crucial part in the subcutaneous absorption processes, namely fibroblasts and endothelial cells, were used. Fibroblasts are the most numerous cells in the connective tissue properly so called. Their function is to produce the fibers and macromolecular constituents of extracellular matrix (including hyaluronic acid). The endothelial cells constitute the cell monolayer that lines the blood vessels and acts as a selective barrier to the passage of molecules from the tissues to the blood.

These studies were conducted in monolayer cell models to determine more directly the ability of each cell line used to capture the Cy5-HyaluSphere nanoparticles. HUVEC endothelial cells and human foreskin fibroblasts (HFF) were used, and absorption was evaluated by flow cytometry and fluorescence microscopy by displaying fluorophore Cy5.

$10^5$ cells per well were plated for 24 hours in a 24-well plate with 500 µL of RPMI to which 10% foetal bovine serum and antibiotics were added. The cells were left to adhere for 24 h in 5% CO2 at 37° C. The culture medium was then aspirated and replaced with fresh medium containing the following concentrations of Cy5-HyaluSphere nanoparticles: 1:10, 1:100, 1:1000 and 1:10000 nanoparticles per cell. The exact number of nanoparticles per cell was calculated with a spectrophotometric method (*J.D. Unciti-Broceta*, et al. 2015, *Scientific Reports* 5, 10091). Cy5-FluoroSpheres were used as controls for the study.

Figure 8:
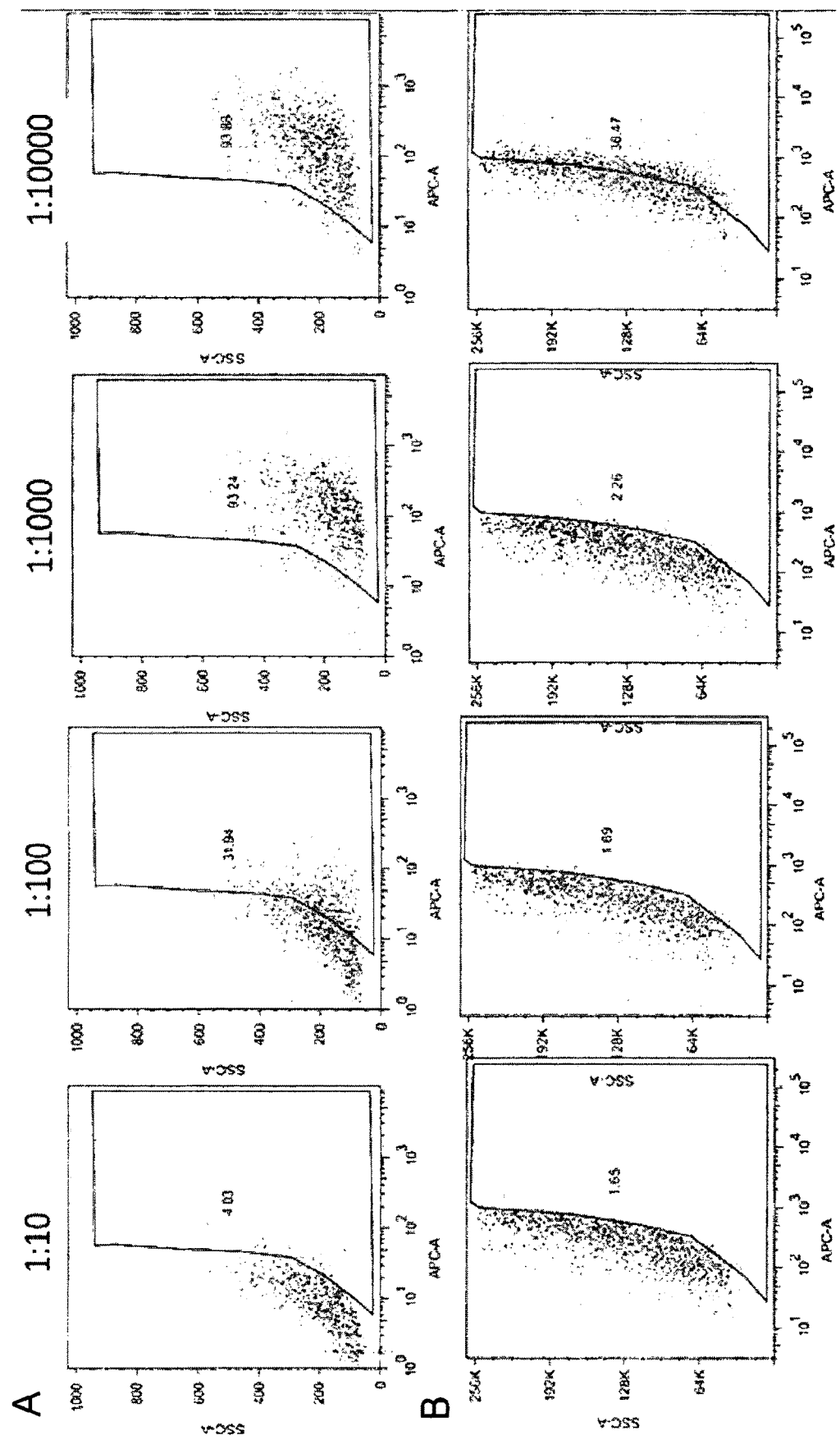
FIG. 8. Flow cytofluorometry data of cell penetration by nanosystems obtained as described in Example 2 on (A) HUVEC and (B) HFF cell lines.

Using a 1:1000 concentration, it was observed that about 100% of HUVEC cells internalize Cy5-HyaluSpheres [FIG. 8A]. In the case of HFF, when the concentration is 1:1000, no internalization of Cy5-HyaluSphere nanoparticles is observed [FIG. 8B]. When the concentration of nanoparticles per cell was increased to 1:10000, it was observed that only 35% of HFF cells internalized the Cy5-HyaluSphere nanoparticles [FIG. 8B]. These results are particularly significant, because they demonstrate that Cy5-HyaluSpheres: 1) are not easily internalized by fibroblasts, and can therefore cross the connective tissue; 2) penetrate the endothelial cells and are easily conveyed into the bloodstream.

Model 2: Cell Penetration in Three-Dimensional (3D) Models

Nanoparticles prepared as described in Example 2 (Cy5-HyaluSpheres) were tested in this study, and nanoparticles conjugated to Cy5 only (Cy5-FluoroSpheres) were used as control. Three-dimensional (3D) cell models that simulate the subcutaneous tissue environment were used. A Matrigel gel (Matrigel® Basement Membrane Matrix, Corning) was used for the study. The composition of said matrix is characterised by the presence of proteins, such as laminin, collagen IV, heparan sulphate proteoglycans, entactin/nidogen glycoprotein, and various growth factors, such as epidermal growth factor, insulin-like growth factor, fibroblast growth factors, tissue plasminogen activators and other growth factors. A concentration of hyaluronic acid was added to the Matrigel for this study. The number of nanoparticles added to the Matrigel was 10000 per cell.

Briefly, a monolayer of endothelial cells (HUVEC) with a concentration of 5000 cells per well was seeded on a monolayer of a type B gelatin solution (SIGMA). The Matrigel was mixed at the ratio of 1:2 with the culture medium, and hyaluronic acid was added at the concentration of 3 mg/mL. When the Matrigel had become semisolid, the Cy5-FluoroSphere nanoparticles (control) and Cy5-HyaluSpheres with a concentration of 10000 nanoparticles per cell were added on the semisolid layer of Matrigel, and incubated for 24 h (in different wells). The internalization efficiency of the Cy5-HyaluSpheres was evaluated by confocal microscopy, evaluating the difference in cell absorption of the nanoparticles after crossing the Matrigel component; only the Cy5-HyaluSpheres cross the Matrigel and are therefore internalized by the HUVEC cells, unlike the controls, which are unable to cross the Matrigel layer, and are therefore not internalized by the HUVEC cells.

Model 3: Cell Penetration in Transwell Models

To evaluate the ability of the nanoparticles, prepared as described in Example 2 (Cy5-HyaluSpheres), to cross the endodermal layer, two experiments were conducted on Transwell® cell culture inserts (Corning). These are permeable support devices which are easy to use to create an environment for cell cultures very similar to the in vivo state.

Briefly, a thick layer of HUVEC endothelial cells was seeded on the insert with 90% confluence to simulate the endothelial layer wherein the cells are closely connected. Subsequently, a layer of Matrigel, mixed with 3 mg/mL of hyaluronic acid, was placed on the cell layer (50000 cells per well). Cy5-HyaluSpheres and Cy5-FluoroSpheres were added on the Matrigel layer and incubated for 72 hours. After the incubation period, the nanoparticles in the lower part of the well (under the insert) were collected, and the number of nanoparticles recovered was measured by flow cytometry. The results demonstrate that the presence of hyaluronidase enables the Cy5-HyaluSpheres to cross the Matrigel layer more easily than the Cy5-FluoroSpheres (FIG. 9A).

Figure 9:
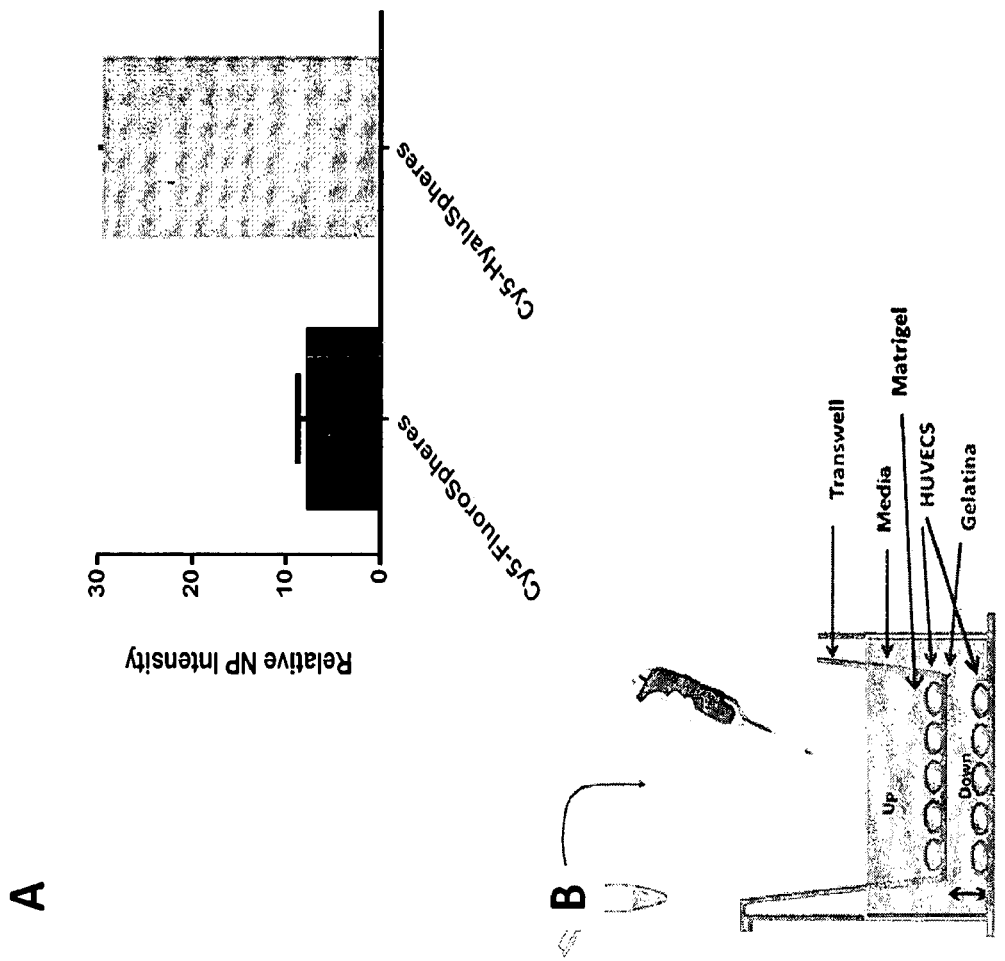
FIG. 9. A) Count of number of Cy5-HyaluSpheres and Cy5-FluoroSpheres present in the lower part of the insert (Transwell). B) In vitro Transwell model with two HUVEC monolayers. C) Fluorescence microscopy of cell penetration by Cy5-HyaluSpheres of the HUVEC monolayer in the lower part of the insert.

In the second experiment, two layers of HUVEC cells were seeded in the insert (over and under it) to test the ability of the Cy5-HyaluSpheres to be internalized by the endothelial cells (under the insert) after crossing the Matrigel layer and the first cell layer [FIG. 9B]. A layer of Matrigel, mixed with 3 mg/mL of hyaluronic acid, was placed on the first layer of HUVEC. Cy5-HyaluSpheres and Cy5-FluoroSpheres were added on the Matrigel layer and incubated for 72 hours. Confocal miscroscopy analysis (FIG. 9C) demonstrated that the Cy5-HyaluSpheres were effectively internalized by the HUVEC cells seeded under the insert after crossing the Matrigel layer with hyaluronic acid and the first cell monolayer.

Example 8

Evaluation of Activity of Nanosystem Prepared as Described in Example 3B

This study evaluated the activity of the drug Doxorubicin and hyaluronidase, both bonded to the nanosystems according to the present invention and prepared as described in Example 3B (hereinafter called Doxo-Hyalusphere).

The cytotoxic activity of Doxo-Hyalusphere was tested on tumour cell lines 4T1 (breast cancer) and A549 (lung cancer), using the in vitro MTT assay.

For the purpose of the test, cell line 4T1 was cultured in RPMI medium (Gibco) and A549 in DMEM (Gibco). 10% FBS (foetal bovine serum, Gibco), 1% L-glutamine (Gibco) and 1% penicillin/streptomycin (Gibco) were added to both culture media at the temperature of 37° C. in the presence of 5% $CO_2$.

The cells were plated in 24-well microplates (Nunc) (50000 cells per well in 500 µl of medium). After 12 hours, 100 µl of culture medium containing the various conditions studied was added to each well:
1) Nanoparticles with PEG (PEG-NP);
2) Nanoparticles with rHyal_Sk (Hyal-NP);
3) Doxorubicin in solution (Free DOX);
4) Doxorubicin bonded to nanoparticles (DOX-NP)
5) Doxo-HyaluSpheres (DOX-Hyal-NP).

The nanoparticle concentrations were established at 40000 per cell, and the plates were incubated for 24 and 96 hours. The species containing doxorubicin were prepared at a concentration equivalent to 3 nM of drug (1.6 ng/mL). The wells were washed with PBS (Phosphate Buffered Saline), and 100 µL of 3-(4,5-dimethylthiazol-2-yl)-2,5-diphenyltetrazolium bromide [(MTT) (0.5 mg/ml in colourless medium)] was then added. The plates were left to incubate at 37° C. in the presence of 5% $CO_2$ for 4 hours. The MTT was then removed, and 100 µL of a solution of Triton X 100, isopropanol and 37% HCl (12M) was added.

Metabolic activity was evaluated after 30 minutes by reading the optical density (OD) with an ELISA Reader (Bio-Rad) spectrophotometer at the wavelength of 570 nm. Each sample was prepared in triplicate, in three independent experiments. The fraction of viable cells was determined on the basis of the ratio between the mean optical density of the treated samples and that of the untreated control sample.

Figure 10:
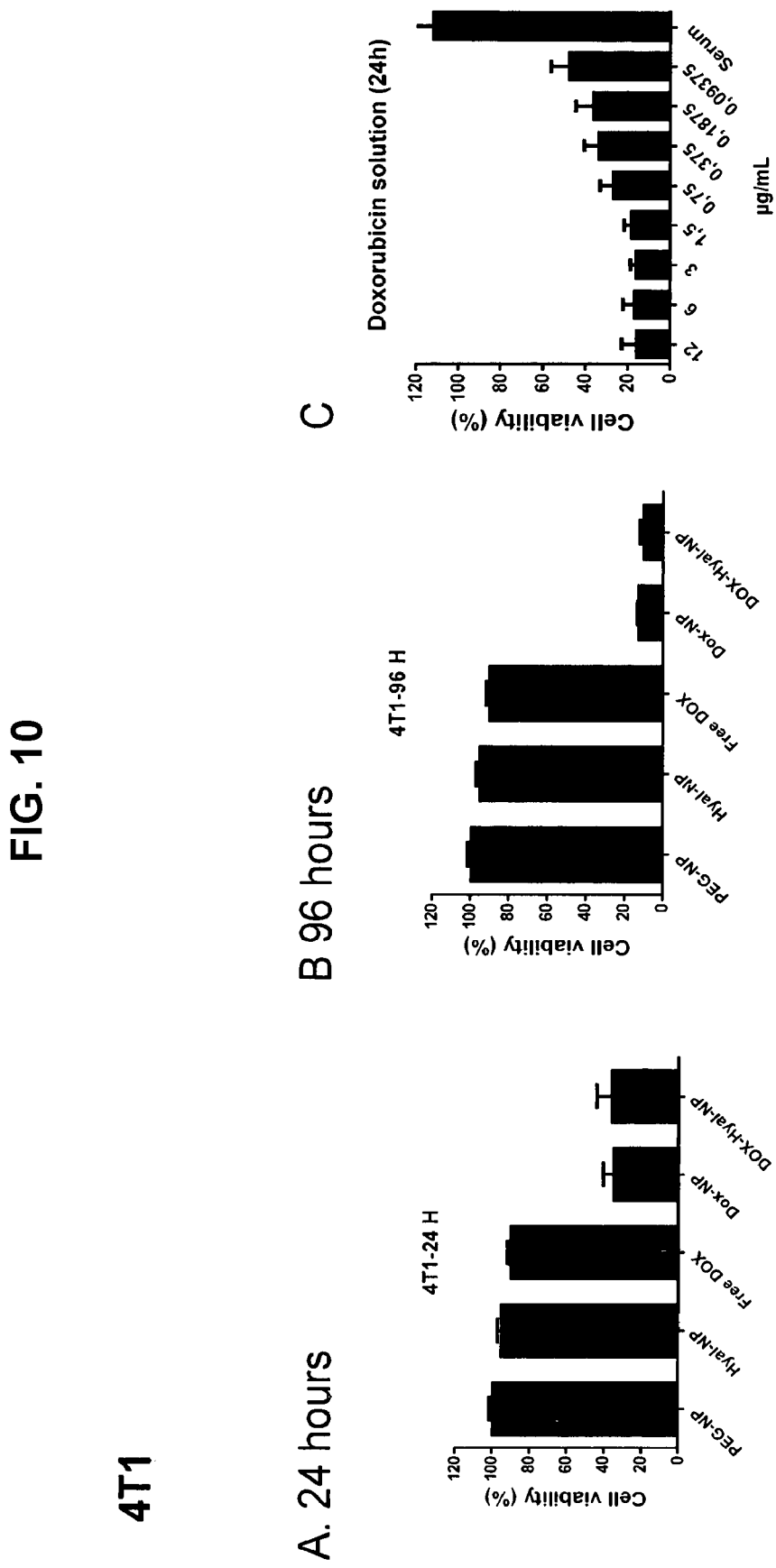
FIG. 10. Cytotoxic activity of doxorubicin covalently bonded to nanoparticles on cell line 4T1.
Figure 11:
FIG. 11. Cytotoxic activity of doxorubicin covalently bonded to nanoparticles on cell line A549.
Figure 11:
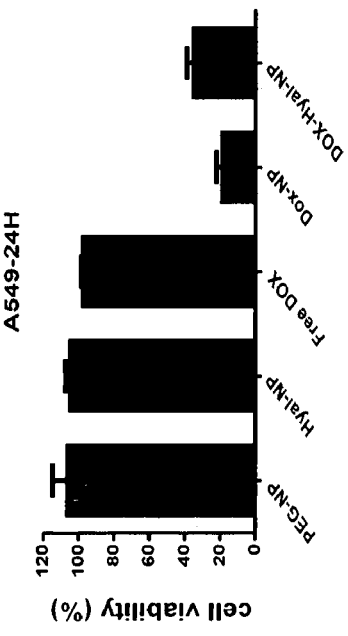
Figure 11:
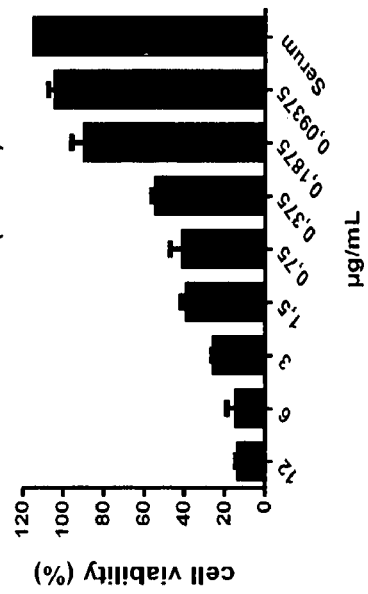

As shown by the graphs in FIGS. 10A and B, tumour cells 4T1 treated with the nanoparticles alone (PEG-NP) and with the nanoparticles conjugated to rHyal_Sk and without medicament (Hyal-NP) do not exhibit any toxicity, maintaining cell viability at around 100% (using cells treated with saline solution as controls). Treatment of the 4T1 cell lines with the free drug (Free-DOX, FIG. 10A-B) did not lead to cell death; however, when the same quantity of drug of the Free-DOX model is bonded to the nanosystem, its ability to kill 4T1 considerably increases, in the case of both Dox-NP and DOX-Hyal-NP, which acquire considerable cytotoxic activity. After 24 hours' treatment tumour cell survival is 34%, and this rate falls to 10% after 96 hours' treatment. Quantitatively identical results were obtained with a quantity of free doxorubicin amounting to 0.75 µg/mL (FIGS. 10A, B, C), i.e. with a far higher dose of medicament. This means that the systems according to the invention are exceptionally efficient and enable doxorubicin to be used at far lower concentrations than those currently known. Similar results were obtained with tumour line A549 (FIG. 11).

The enzymatic activity of the resulting nanosystem was measured by turbidimetric determination conducted according to the protocol reported in Example 5. $2 \times 10^9$ nanoparticles, corresponding to the activity of 1 U of hyaluronidase, were used for the study. The results demonstrate that the enzyme retains 97.5% hyaluronidase activity. This confirms the efficiency of the system and demonstrates the high stability of rHyal_Sk, even after the coupling process used to prepare the nanosystems described herein.

It is therefore obvious that the two constituents covalently bonded to the same nanoparticle maintain their respective anti-tumoral activity and enzymatic activity intact.

Example 9

Evaluation of Activity of Nanosystem Obtained as Described in Example 4B

A nanosystem containing rHyal_Sk and Anti-EGF receptor antibody (Ab-HyaluSpheres) was prepared as described in Example 4B.

The enzymatic activity of the nanosystem was measured by turbidimetric determination conducted according to the protocol reported in Example 5. These results demonstrate that the enzyme retains a hyaluronidase activity of around 98.8±2.5%. This confirms the high stability of rHyal_Sk after the coupling process used to prepare the nanosystems obtained as described in Example 4B.

Conjugation to the anti-EGFR monoclonal antibody was validated with an agarose gel electrophoresis test (Lee J. et al, 2010, Bioconjugate Chem., 21, 940-946).

Briefly, 10 μL of sample [(8 uL of nanosystems (Example 4) and 2uL of 5× DNA Loading Buffer Blue (Bioline)] are loaded onto 0.8% agarose gel and immersed in a buffer consisting of 89 mM tris, 89 mM borate and 2 mM EDTA, pH 8.0 (TBE). The samples are run for 30 minutes under a voltage of 70 mV. The gel was stained according to standard protocols with Coomassie Blue at the end of the gel electrophoresis run. The colocalization of the nanosystems stained with Coomassie Blue indicates coupling of the nanosystems with the anti-EGFR monoclonal antibody.

Figure 12:
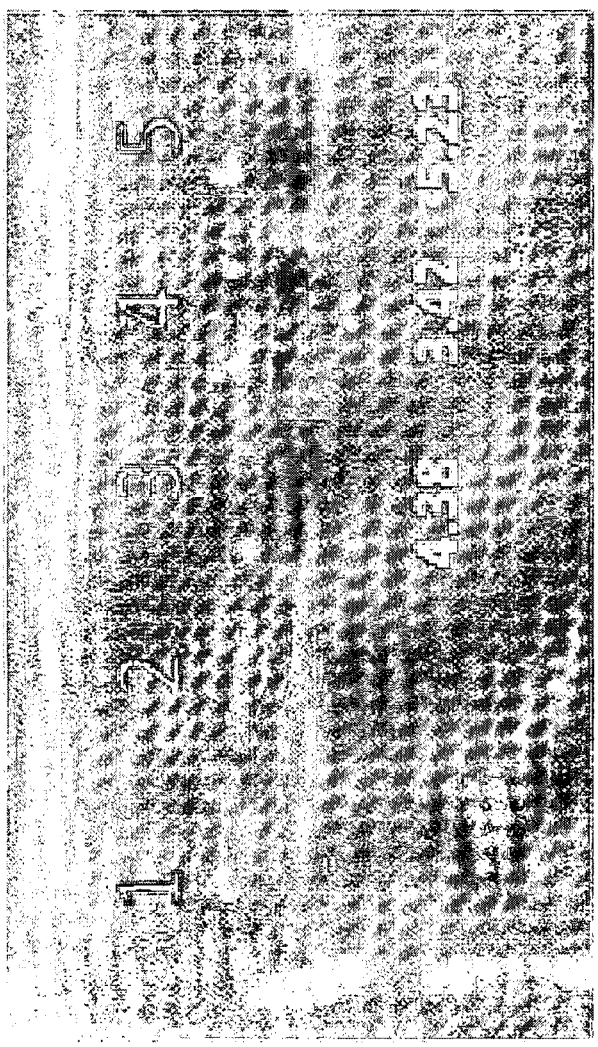
FIG. 12. Validation of conjugation to monoclonal antibody on nanosystems obtained as described in Example 4B (agarose gel electrophoresis test).

The method is based on the non-motility of the nanosystems in agarose gel. The nanosystems are unable to move from the wells, whereas the free antibodies migrate towards the negative electrode because they have a slight positive charge. The efficiency of conjugation was therefore evaluated by analyzing the preservation of the antibody in the gel well. FIG. 12 shows the gel obtained, reading of which demonstrates effective conjugation of Ab to the nanoparticles (lines 3-5, FIG. 12). The two controls were line 1: Ab in solution without coupling to the nanoparticles; line 2: nanoparticles without Ab.

Example 10

Evaluation of Activity of Nanosystem Obtained as Described in Example 4C

A nanosystem containing a trifunctionalization with a fluorophore, rHyal_Sk and an anti-EGF receptor antibody (Cy5-Ab-HyaluSpheres) was prepared as described in Example 4C.

The enzymatic activity of the nanosystem was measured by turbidimetric determination conducted according to the protocol reported in Example 5. These results demonstrate that the enzyme retains a hyaluronidase activity of around 98.8%. This confirms the efficiency of the system and demonstrates the high stability of rHyal_Sk, even after the trifunctionalization process obtained as described in Example 4C.

Figure 13:
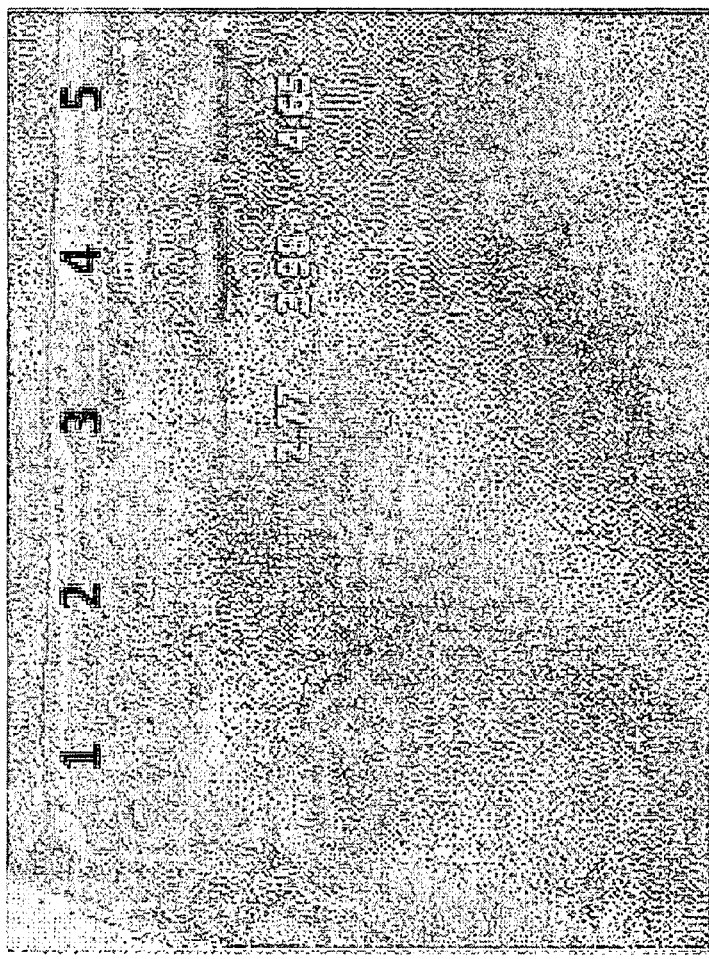
FIG. 13. Validation of conjugation to monoclonal antibody on nanosystems obtained as described in Example 4C (agarose gel electrophoresis test).

The efficiency of conjugation of the antibody to the nanosystem was evaluated by agarose gel electrophoresis and staining with Coomassie Blue, as described in Example 9. FIG. 13 shows the results obtained: line 1) (control): free Ab; Line 2 (control) only corresponds to the nanoparticles; Lines 3-5: different concentrations of Ab conjugated to the nanoparticles. The most intense bands were observed in wells 3, 4 and 5, which correspond to a gradient of increasing concentrations. The bands were quantified by imaging analysis using ImageJ software (National Institutes of Health).

The coupling of the fluorophore and the selectivity of the AntiEGFR-Cy5-HyaluSpheres was studied by monitoring their cell absorption with flow cytometry. The study was conducted by comparing the internalization results of the AntiEGFR-Cy5-HyaluSphere nanoparticles on tumour cell lines A549 and H520. Cell line A549 presents over-expression of the EGFR receptor, and line H520 presents low expression of the EGFR receptor. FIG. 14 shows the flow cytometry results. The AntiEGFR-Cy5-HyaluSpheres exhibited (as expected) a greater ability to penetrate the A549 cells with over-expression of EGFR receptor (about 99%) and a lower ability to penetrate the line with low expression of the receptor (about 22%). This demonstrates that the antibody selectively guides the penetration of the nanoparticles towards the EGFR antigen (FIGS. 14B and C). The Cy5-HyaluSpheres nanoparticles were used as control. Examples of possible fields of application of the invention include:

a) Immunostaining (in vitro): the nanosystems are conjugated to fluorophores and specific directional antibodies and with hyaluronidase, which increases their permeabilization when added to cell cultures. The antibodies guide the nanosystems to molecular recognition, bonding to the antigen or to target regions containing the antigen.

In this way said regions are highlighted by the fluorophores;

b) Single particle-tracking (in vivo): nanosystems conjugated to fluorophores and binders specific for membrane receptors (antibodies) bond to them outside the cell and make them visible. The hyaluronidase allows them to enter the bloodstream by means of subcutaneous administration. The movements and trajectories of the receptor can be monitored by displaying the labelled nanosystems.

c) Targeted pharmacological treatment, specifically antitumoral treatment: in this case the nanosystem transports an antitumoral drug. If the recognition of the tumour cells takes place via membrane receptors, antibodies can be used to ensure that the nanosystem is preferably directed to sick cells wherein the receptors are over-expressed. The systems according to the invention are particularly suitable for tumors characterised by an accumulation of hyaluronic acid in the tissues. Tumors that produce an abnormal accumulation of hyaluronic acid which, by compressing the surrounding vessels, prevents or at least slows the transport of the drugs administered to the target site, particularly affect organs such as the breast, pancreas, colon and prostate. The excess hyaluronic acid accumulated also provides the tumour with an excellent growth substrate. In such situations it is essential to have a system that delivers the drug and simultaneously enables it to act completely, by eliminating a major mechanical and biological obstacle. When tumour cells are recognised, the hyaluronidase increases their permeabilization by destroying the layers of hyaluronic acid that protect the tumour environment. After crossing the coating of hyaluronic acid, the nanosystems release the antitumoral medicament, which thus acts more effectively. In this type of application, the nanosystem acts as directional carrier, giving the antitumoral medicament a selective action. Moreover, the presence of hyaluronidase can allow subcutaneous administration.

The nanosystems described herein therefore present the advantages of being inert, biocompatible, and easily synthesized and functionalised with any type of molecule. They also retain intact the characteristics of the molecules bonded to them and, in the case of some molecules, allow alternatives to the conventional administration routes to be used.

The nanosystems according to the invention therefore represent multipotent, flexible, reproducible, easily scalable systems, which can be used as molecular transporters for diagnostic, prognostic and therapeutic purposes.

The invention claimed is:

1. A nanoparticle system comprising polystyrene nanoparticles, wherein the nanoparticles are 200 nm in size, and covalently bonded to a heterocarbon chain; a hyaluronidase; and one or more active molecules covalently bonded to said heterocarbon chain, wherein
    the polystyrene nanoparticles covalently bonded to a heterocarbon chain are formed by reacting amino-functionalized polystyrene nanoparticles with N-Fmoc-N"-succinyl-4,7,10-trioxa-1,13-tridecanediamine to covalently bond primary amines on the polystyrene to functional groups on the heterocarbon chain;
    the hyaluronidase is recombinant hyaluronidase rHyal_Sk; and
    the one or more active molecules are an antibody and optionally a fluorophore, and wherein the recombinant hyaluronidase rHyal_Sk is bonded to the heterocarbon chain via diethyl squarate.

2. The nanoparticle system according to claim 1 wherein the covalent bonds between the functional groups of the heterocarbon chain and one or more active molecules are mediated by glutaraldehyde, maleimide, active esters, disulphide groups, squaric acid or derivatives thereof.

3. A pharmaceutical composition comprising the nanoparticle system of claim 1 in admixture with pharmaceutically acceptable excipients.

4. The pharmaceutical composition according to claim 3 in lyophilized form for reconstitution, or in aqueous suspension or gel form.

5. The pharmaceutical composition according to claim 3 for subcutaneous, intradermal, intrathecal, intramuscular, intraperitoneal, intravenous, intra-arterial, transdermal, transcutaneous, transmucosal or inhalatory administration.

6. A nanoparticle system comprising polystyrene nanoparticles, wherein the nanoparticles are 200 nm in size, and covalently bonded to a heterocarbon chain; a hyaluronidase; and one or more active molecules covalently bonded to said heterocarbon chain, wherein
    the polystyrene nanoparticles covalently bonded to a heterocarbon chain are formed by reacting amino-functionalized polystyrene nanoparticles with N-Fmoc-N"-succinyl-4,7,10-trioxa-1,13-tridecanediamine to covalently bond primary amines on the polystyrene to functional groups on the heterocarbon chain;
    the hyaluronidase is recombinant hyaluronidase rHyal_Sk; and
    the one or more active molecules are an antibody and optionally a fluorophore, and wherein the recombinant hyaluronidase rHyal_Sk is bonded to the heterocarbon chain via diethyl squarate,
    wherein the heterocarbon chain does not contain a free charge, and
    wherein the one or more active molecules are bound to only one heterocarbon chain.

* * * * *